(12) United States Patent  
Goode

(10) Patent No.: US 6,687,548 B2  
(45) Date of Patent: Feb. 3, 2004

(54) APPARATUS FOR REMOVING AN ELONGATED STRUCTURE IMPLANTED IN BIOLOGICAL TISSUE

(75) Inventor: Louis B. Goode, Cranberry Township, PA (US)

(73) Assignee: Cook Vascular Incorporated, Leechburg, PA (US)

(*) Notice: Subject to any disclaimer, the term of this patent is extended or adjusted under 35 U.S.C. 154(b) by 259 days.

(21) Appl. No.: 09/859,555

(22) Filed: May 17, 2001

(65) Prior Publication Data

US 2002/0007204 A1 Jan. 17, 2002

(51) Int. Cl.[7] .................................................. A61N 1/05
(52) U.S. Cl. ....................................... 607/119; 606/108
(58) Field of Search ................................ 607/115, 119, 607/122; 606/1, 108

(56) References Cited

U.S. PATENT DOCUMENTS

| 4,706,671 | A | | 11/1987 | Weinrib |
| 4,791,939 | A | | 12/1988 | Maillard |
| 4,943,289 | A | | 7/1990 | Goode et al. |
| 4,988,347 | A | | 1/1991 | Goode et al. |
| 5,011,482 | A | | 4/1991 | Goode et al. |
| 5,013,310 | A | | 5/1991 | Goode et al. |
| 5,207,683 | A | | 5/1993 | Goode et al. |
| 5,549,615 | A | | 8/1996 | Hocherl et al. |
| 5,632,749 | A | | 5/1997 | Goode et al. |
| 5,666,968 | A | * | 9/1997 | Imran et al. ................. 600/585 |
| 5,769,858 | A | | 6/1998 | Pearson et al. |
| 6,136,005 | A | | 10/2000 | Goode et al. |
| 6,167,315 | A | * | 12/2000 | Coe et al. ................... 606/108 |
| 6,231,564 | B1 | * | 5/2001 | Gambale ..................... 604/528 |

* cited by examiner

Primary Examiner—George R. Evanisko  
(74) Attorney, Agent, or Firm—Brinks Hofer Gilson & Lione

(57) ABSTRACT

Disclosed is a lead removal apparatus for removing an implanted pacemaker or defibrillator lead from the heart. The lead removal apparatus includes a proximal handle that further includes a proximal portion, such as an elongate section of intertwined wire, having a compact, pre-formed first configuration, such as one or more coiled loops. The compact shape permits the operator to utilize the proximal portion without requiring the assistance of a second person to help keep it within the sterile field during a procedure. The operator is thus able to constrain or uncoil the proximal portion into a second configuration that is sufficiently straight such that a medical device, such as a dilator sheath, can be advanced thereover to help separate the lead from scar tissue along the vein path. The proximal portion may include sufficient resiliency to substantially return to the first configuration once the sheath has been advanced.

28 Claims, 20 Drawing Sheets

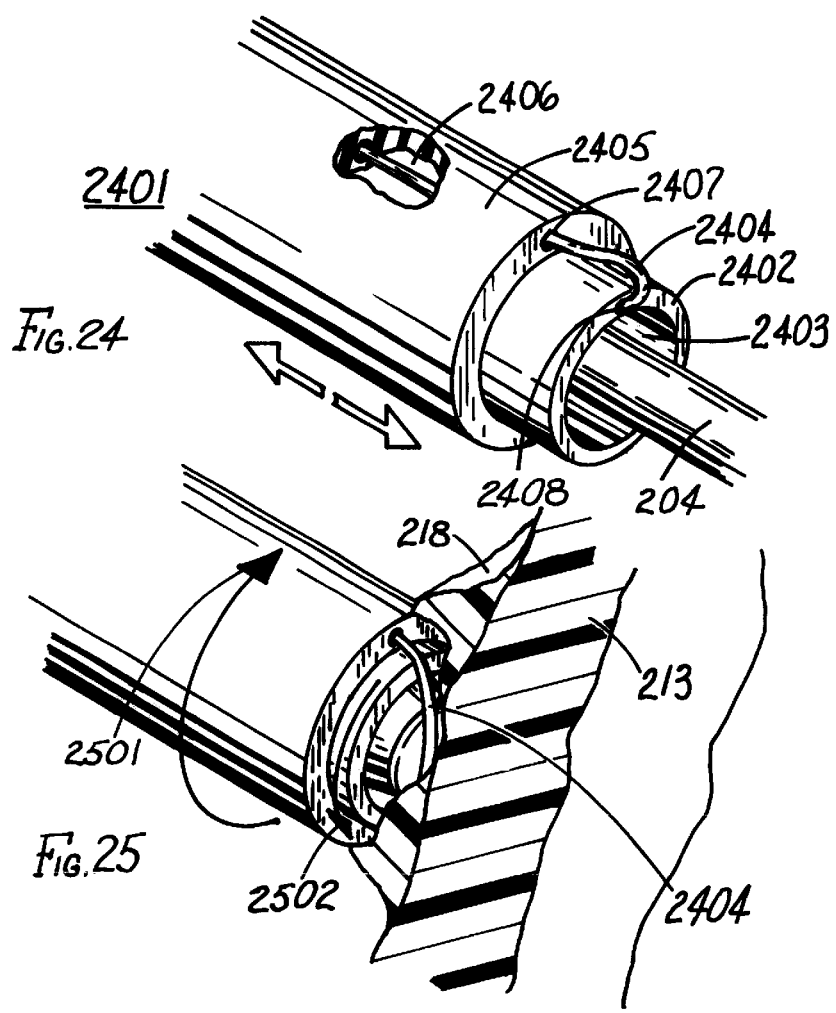
Fig. 24
Fig. 25
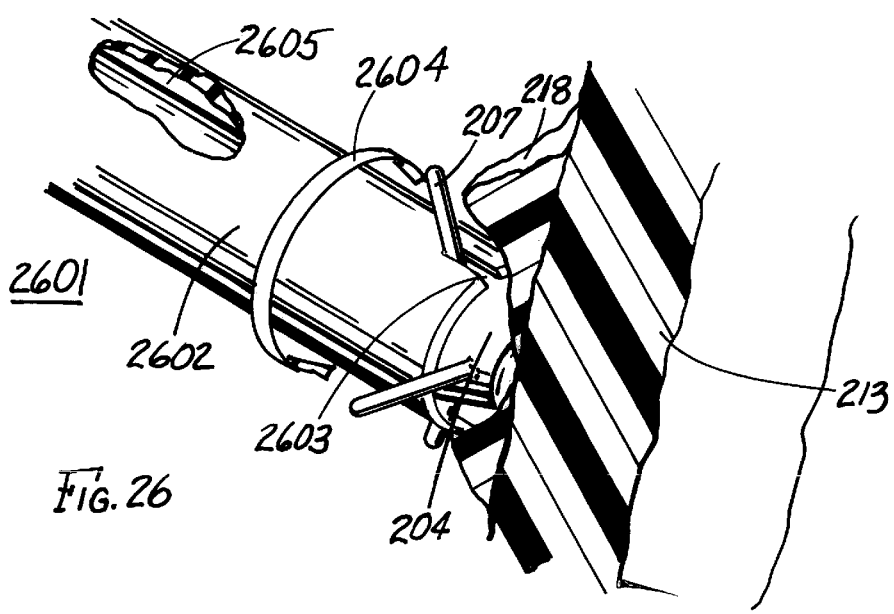
Fig. 26

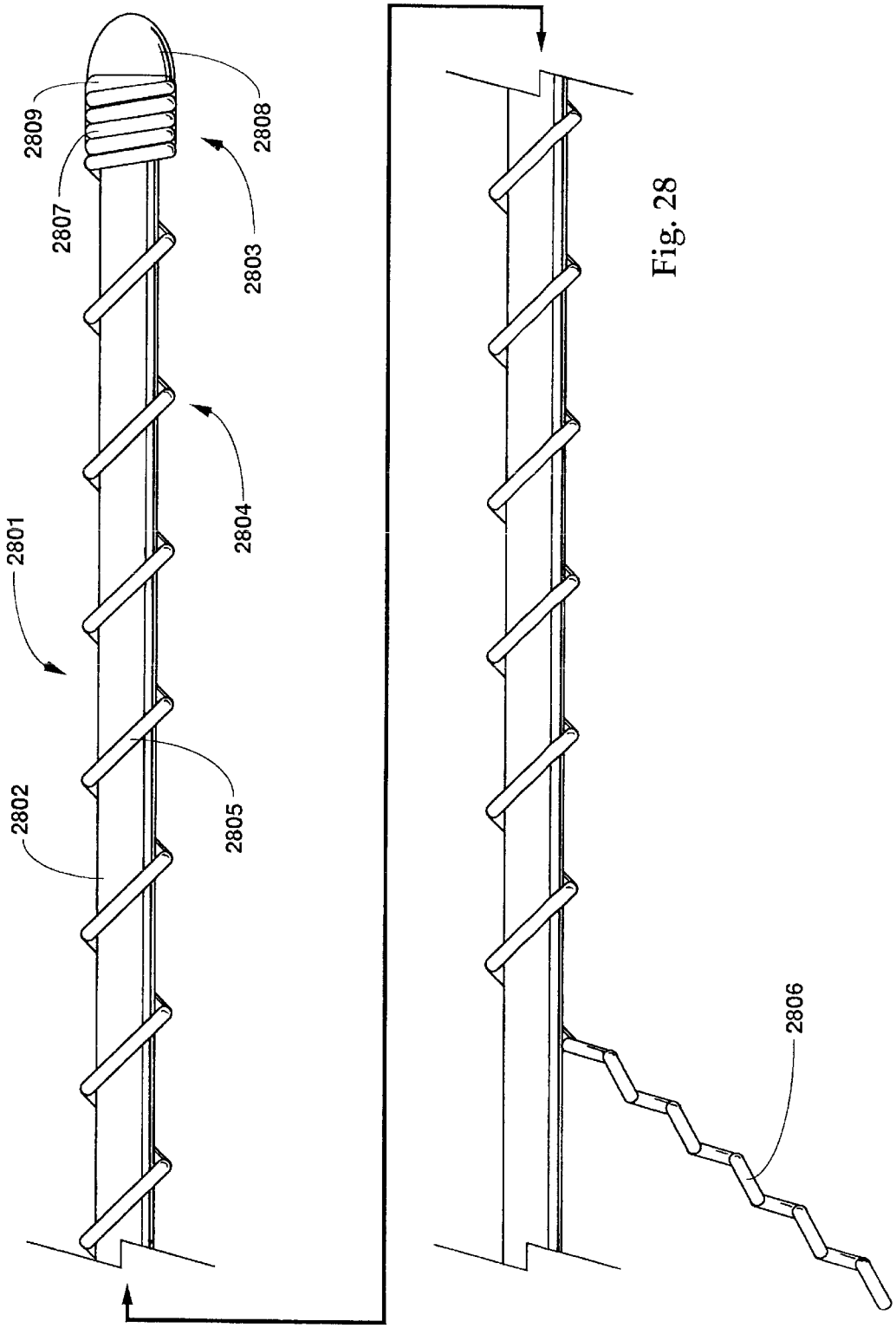

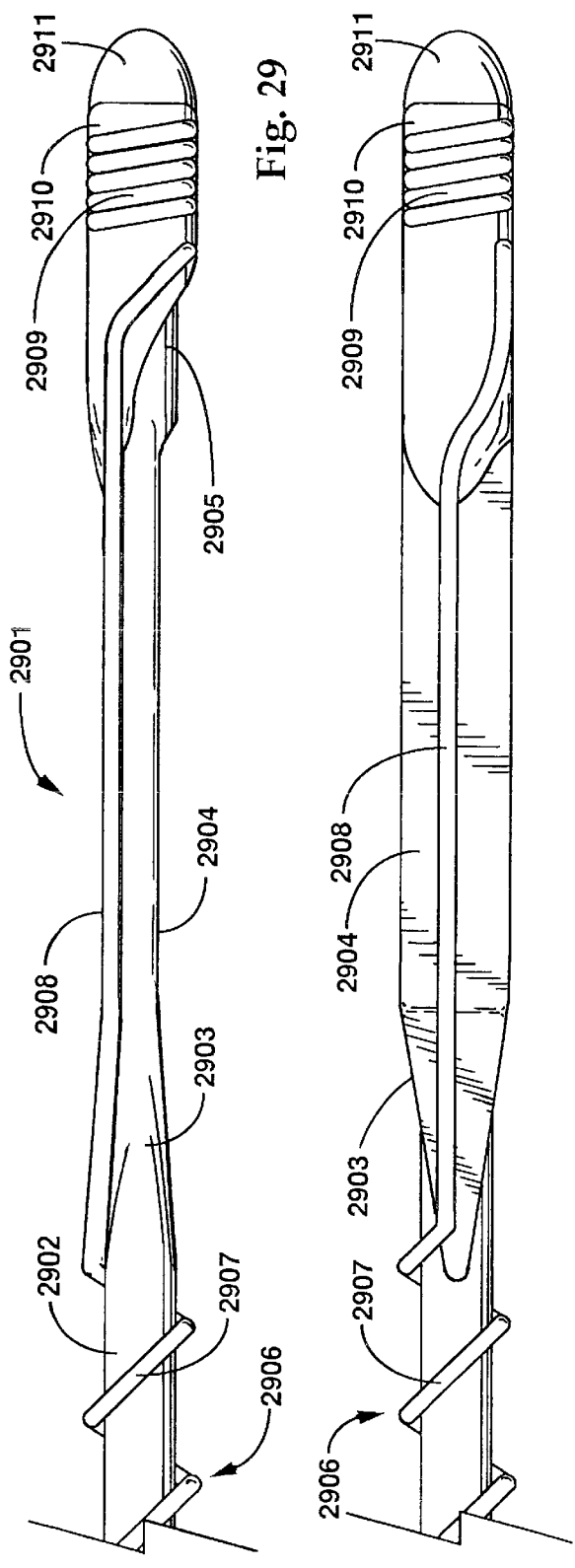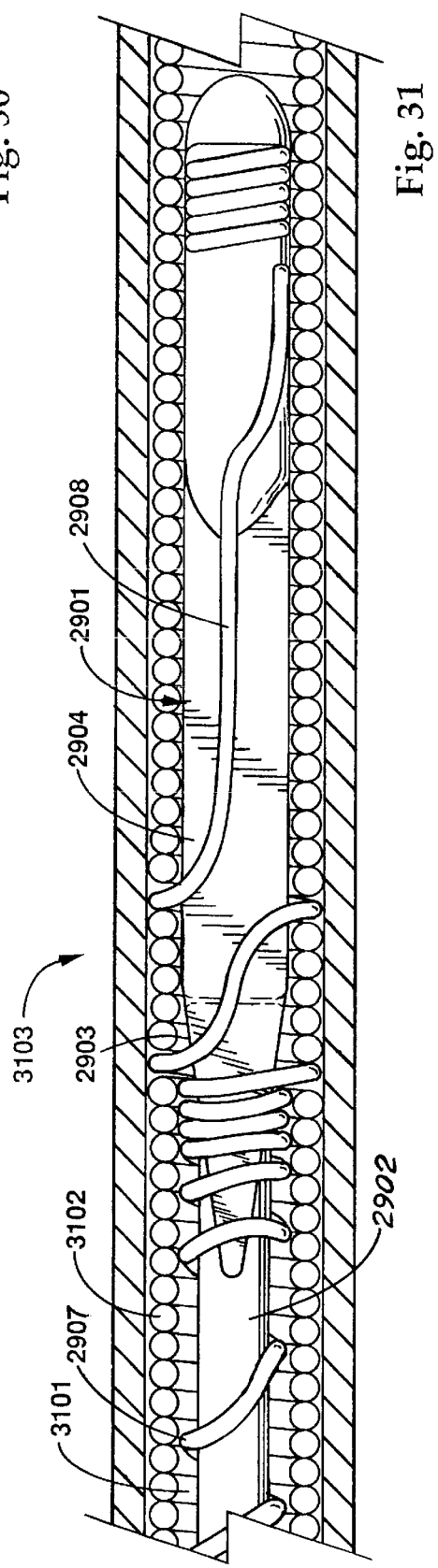

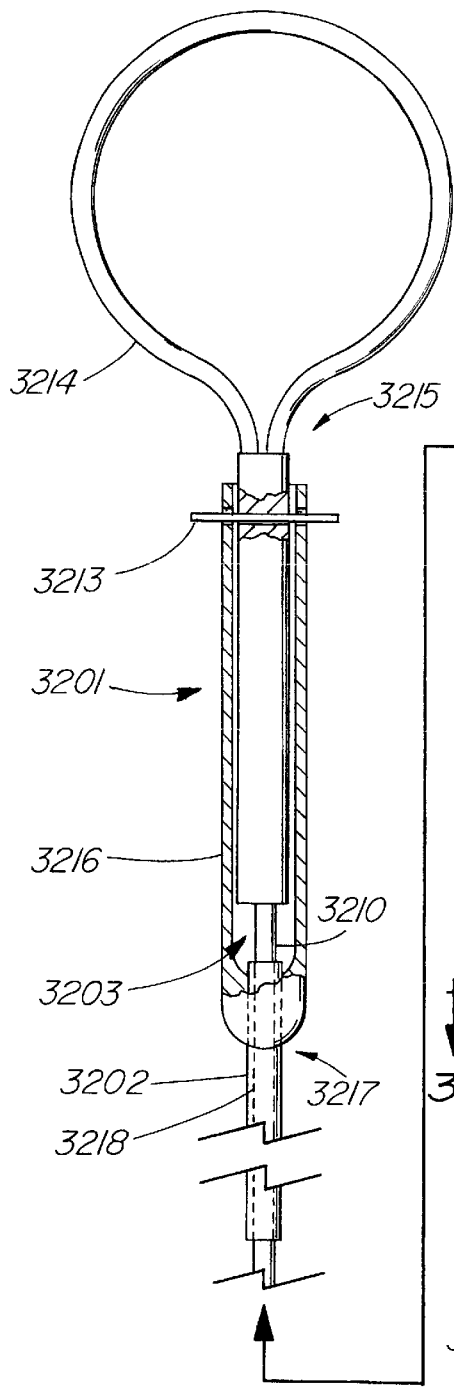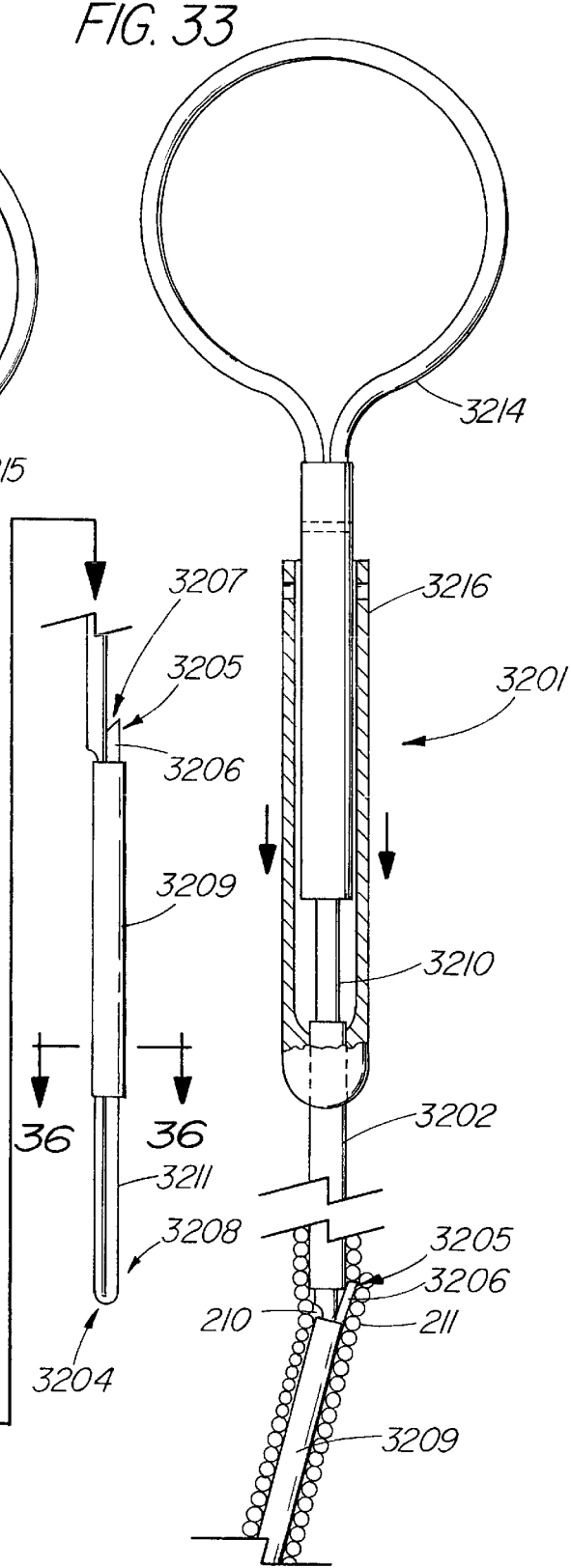

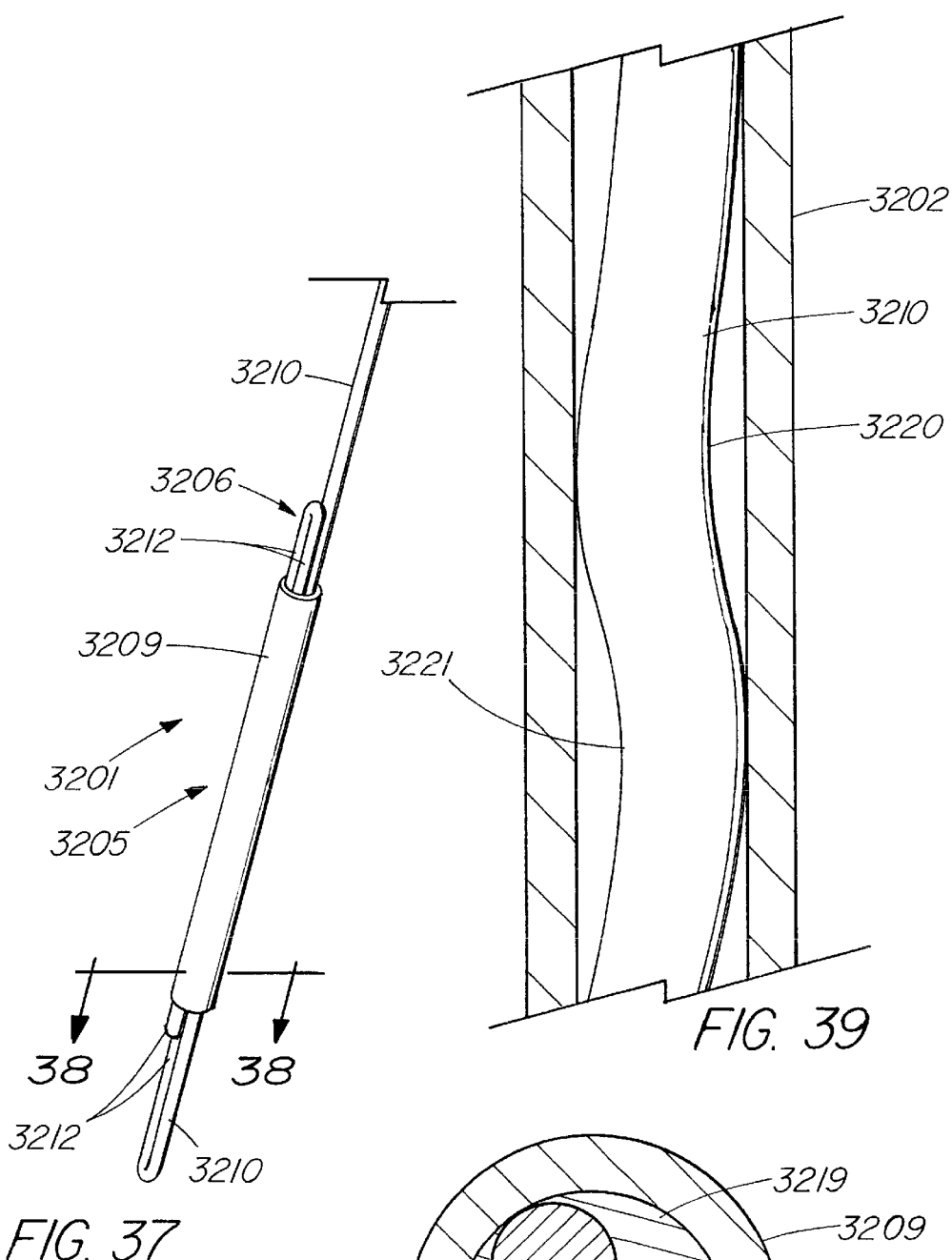
FIG. 37
FIG. 39
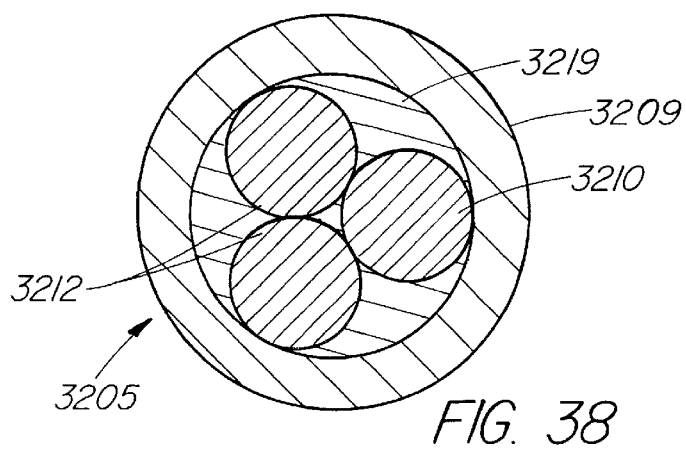
FIG. 38

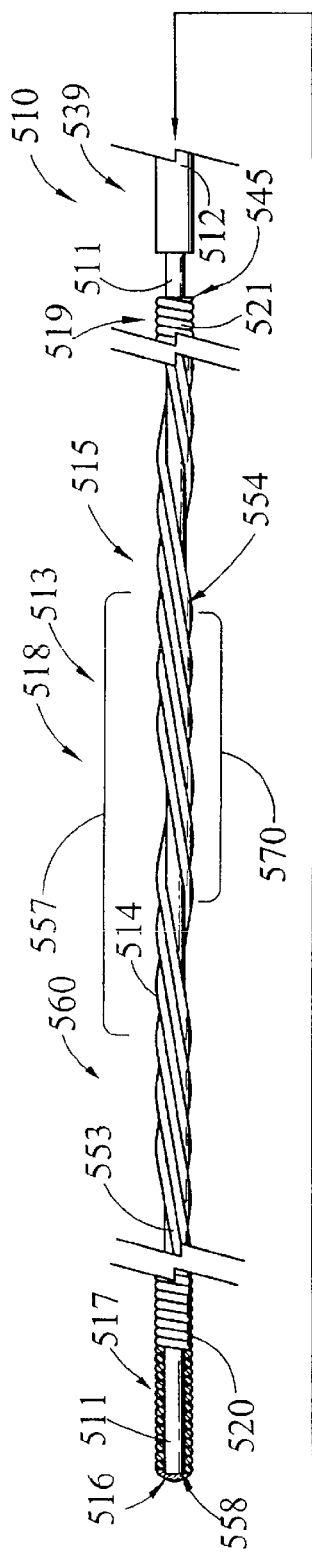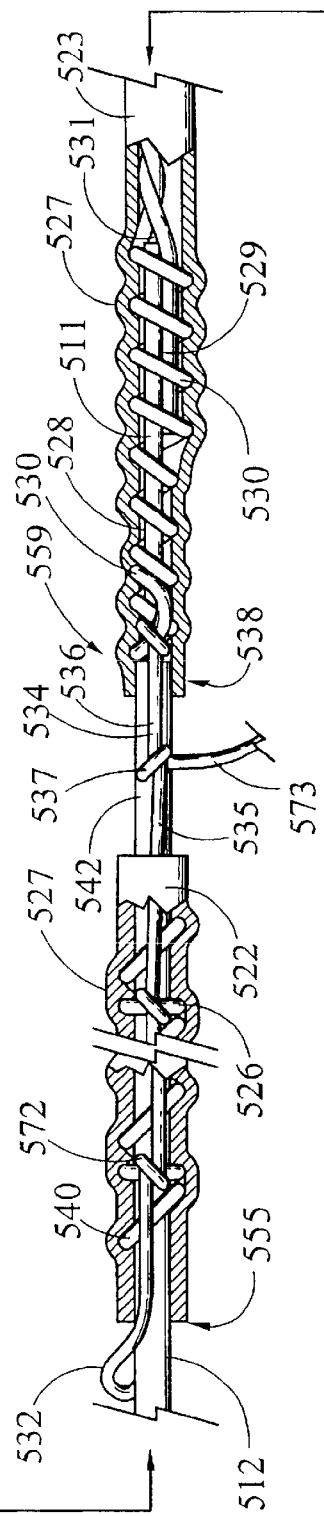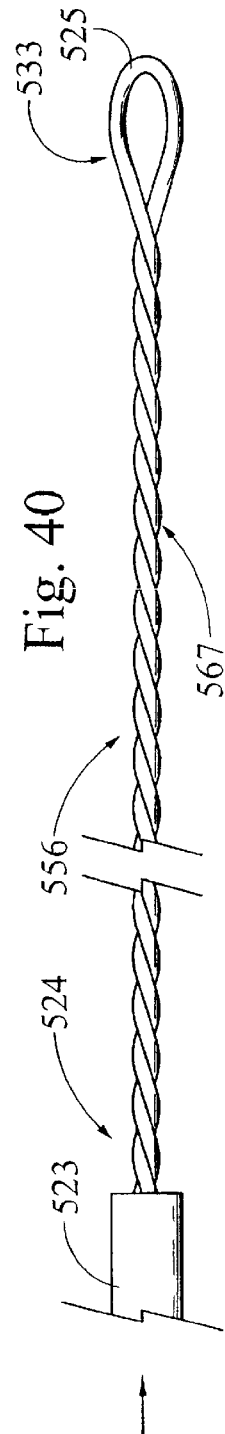
Fig. 40

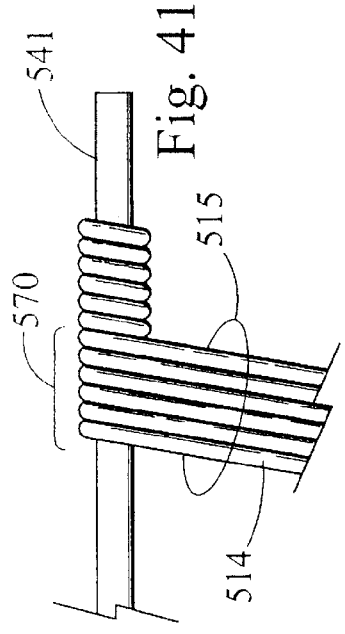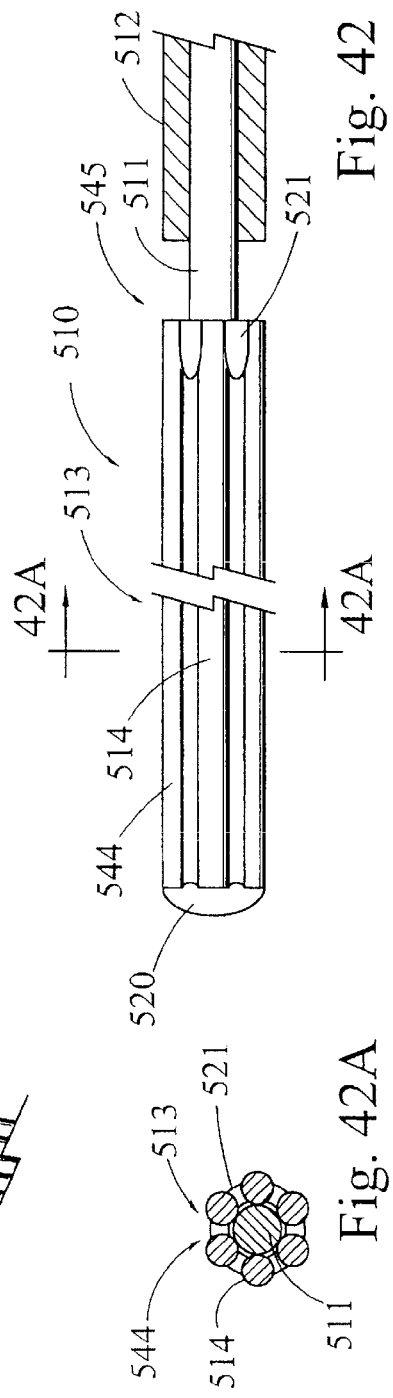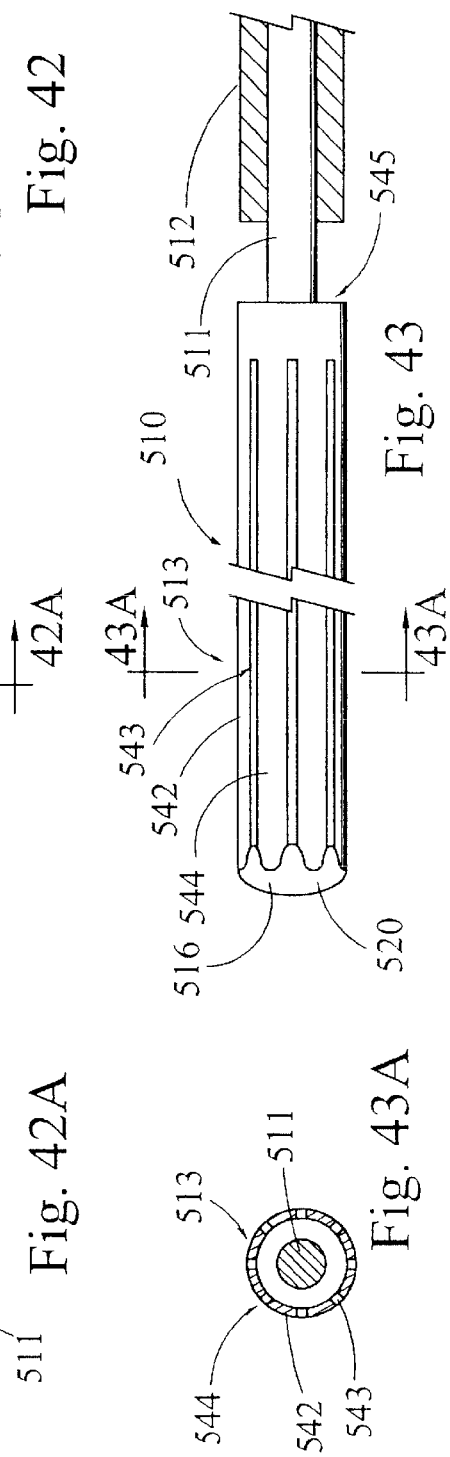

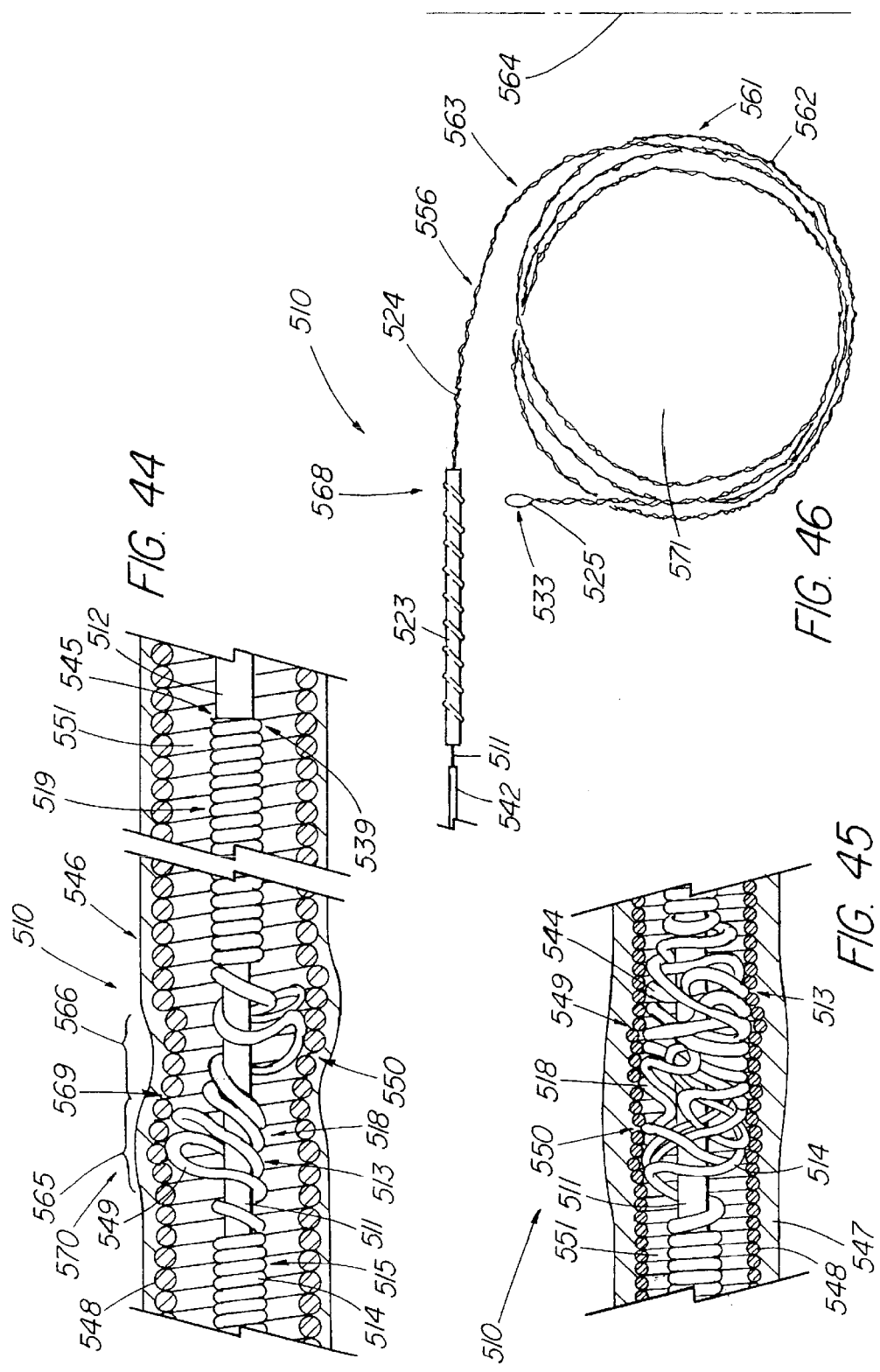

APPARATUS FOR REMOVING AN ELONGATED STRUCTURE IMPLANTED IN BIOLOGICAL TISSUE

TECHNICAL FIELD

This invention relates to elongated structures, such as a catheter implanted in tissue or an electrical pacemaker or defibrillator lead implanted in or on the heart and, particularly, to apparatus for removing such elongated structures implanted in biological tissue.

BACKGROUND OF THE INVENTION

A heart pacemaker is generally implanted subcutaneously in the chest wall along with a coiled structure such as an electrical wire coil lead for conducting electrical signals such as stimulating and sensing signals between the pacemaker and the heart. The lead is surgically implanted through a vein leading to a cavity of the heart. A typical lead includes one or more helical wire coils having a hollow inner passageway that extends the entire length of the wire coil. The coiled structures are positioned in the lead either coaxially or laterally. The wire coils are surrounded by an insulating material such as a flexible tube, sheath, or coating comprising, for example, silicone or polyurethane for insulating the wire coils from body fluids as well as each other. However, one problem is that, over time, fibrotic tissue commonly encapsulates the pacemaker lead especially in areas where there is low velocity blood flow. When small diameter veins through which the lead passes become occluded with fibrotic tissue, separating the lead from the vein is difficult and causes severe damage or destruction of the vein. Furthermore, the separation is usually not possible without restricting or containing the movement of the pacemaker lead.

In most cases, the useful life of a pacemaker lead lasts for many years. However, should the pacemaker lead become inoperative or should another heart lead be desired, the existing pacemaker lead is typically left in place, and a new pacemaker lead is implanted. One problem with leaving an implanted lead in place, particularly in the heart, is that the lead actually restricts the operation of the various heart valves through which the lead passes. If several leads passing through a heart valve are left in place, the operation of the heart valve and the efficacy of the heart is significantly impaired.

Another problem associated with leaving a pacemaker lead in place, particularly in blood vessels, is that an infection may develop in or around the lead, thereby requiring surgical removal. Surgical removal of the lead from the heart often involves open heart surgery with accompanying complications, risks, and significant cost.

One method for transvenous removal of a pacemaker lead involves a prior art heart lead removal tool that utilizes a hollow, rigid tube and a beveled rod tip for engaging and deforming the coiled structure of the heart lead. However, when the lead cannot be removed because of some complication, a serious problem is that the tip of the tool is locked in place and cannot be removed from the lead. As a result, the tool and lead must be surgically removed. Furthermore, the rigid tube of the tool can easily puncture a blood vessel or, even worse, a heart cavity wall.

Another method is to transvenously extract the lead manually without the aid of a tool. Such method is possible only when the lead has not been encapsulated in or restricted by a blood vessel. Even then, this method has a number of problems. First, when the polyurethane or silicon insulation surrounding the wire coil is damaged, the insulation can sever and cause the coiled structure of the lead to unwind and possibly to damage the heart and surrounding blood vessels. Secondly, when both the coiled structure and insulation are severed in the heart or a blood vessel, surgical removal is required. Thirdly, most pacemaker leads typically include tines or a corkscrew at the tip or a conically shaped tip for securing the distal end of the pacemaker lead to a heart cavity wall. For fibrotic tissue that has encapsulated the tip, unaided manual removal of the heart lead from the heart cavity wall may cause an inward extension or inversion of the wall, or even worse, permanent damage to the heart such as tearing a hole in the heart cavity wall.

There a several different systems for lead removal that involved advancing a stylet into the coiled electrode and securing the electrode near the tip of the lead to facilitate its removal. The LEAD EXTRACTION™ System (Cook Vascular Inc., Leechburg, Pa., described U.S. Pat. No. 4,988,347, entitled "Method and Apparatus for Separating a Coiled Structure from Biological Tissue", Filed Nov. 9, 1988, and related subsequent patents) is particularly well-suited for the removal of a pacemaker lead implanted in the heart and encapsulated in vessels connecting with the heart. Others devices by Vascomed and Spectranetics have entered the market in the U.S. and/or Europe. While the use of a radially expandable wire coil at the distal end of a stylet is an effective method of securing the pacemaker lead near the electrode tip, failure to engage has been observed in a number of cases. In an expandable wire coil system, correct sizing of the lead coil is critical prior to introduction of the locking stylet. Nevertheless, behavior of the wire coil during expansion can be unpredictable so that even when the correct locking stylet is selected, adequate engagement with the lead coil often cannot be achieved, or the two can separate during traction to free the lead. While often this may occur due to improper locking technique on the part of the physician, often the failure is purely mechanical. Many times, a second locking stylet can be used successfully, but this results in increased material costs and risk to the patient due to the lengthening of the procedure.

Another disadvantage of currently available systems is that array of different sized stylets must be used for the wide range of pacemaker electrode sizes, normally 0.016 to 0.032'". Having to properly size the coil for selection of the optimal stylet adds time, cost, and the potential for error to the procedure. What is needed is a single locking stylet that can expand to engage and remove any standard pacemaker lead, regardless of the electrode coil size.

SUMMARY OF THE INVENTION

The foregoing problems are solved and a technical advance is achieved with illustrative lead removal apparatus for removing an implanted, cardiac pacemaker lead. The pacemaker lead includes, as previously suggested, a coiled structure such as an electrical wire coil for conducting electrical signals between the pacemaker and the heart. This coiled structure typically has a hollow inner passageway that extends longitudinally therethrough. The wire coil is surrounded by insulating material for insulating the wires from body fluids. The lead removal apparatus includes control means having a distal end for insertion into the passageway of the coiled structure. The lead removal apparatus also includes expandable means positioned proximate the distal end of the control means. The expandable means also has an expanded position in the coiled structure passageway for securing the control means to the coiled structure for removal of the implanted lead from the heart.

In one aspect, the control means comprises actuator means for expanding the expandable means to the expanded position when the expandable means is positioned in the passageway of the coiled structure. The expandable means also includes a relaxed position for positioning the lead removal apparatus in the coiled structure passageway.

In another aspect, the control means includes an outer tube and an actuator rod insertable through the outer tube. The expandable means includes a barb positioned proximate the distal end of the outer tube. When the actuator rod is positioned proximate the distal end of the outer tube, the rod expands the barb to the expanded position.

In another aspect, the expandable means includes a slotted sleeve positioned between the distal ends of the outer tube and the actuator rod. The ends of the tube and rod engage the slotted sleeve when expanding the slotted sleeve to an expanded position, which hooks into the coiled structure for securing the actuator rod to the coiled structure. The distal ends of the rod and the outer tube are beveled for easing expansion of the slotted sleeve when the actuator rod is withdrawn from the outer tube.

In still another aspect, the expandable means includes an expandable pliable material sleeve between the distal ends of the outer tube and the actuator rod. The pliable material sleeve comprises, for example, a pliable material such as synthetic rubber and the like, which expands in a radial direction when compressed between the distal ends of the outer tube and the actuator rod to frictionally engage the coiled structure and secure the outer tube and actuator rod thereto. In another configuration, the pliable material sleeve has an outside dimension greater than the coiled structure passageway when the sleeve is in a relaxed position. The sleeve is stretched between the distal ends of the outer tube and actuator rod to reduce its outer diameter, which is then insertable into the coiled structure passageway.

In yet another aspect, the expandable means of the lead removal apparatus includes projection means proximate a distal end of the outer tube for hooking into the coiled structure. The control means further includes a stylet for engaging and urging the projection means into the coiled structure when positioned in the coiled structure passageway.

The lead removal apparatus may also be characterized as comprising tube means having a distal end for inserting into the passageway of the coiled structure, expansion means positioned proximate a distal end of the tube means for hooking into the coiled structure of the pacemaker lead; and stylet means insertable into the tube means for engaging the expansion means. As previously suggested, the tube means includes an outer tube having a passageway extending longitudinally therethrough. The stylet means includes a wire extending through the outer tube passageway. And the expansion means includes a projection proximate the distal end of the outer tube hooking into the coiled structure when positioned in the coiled structure and expanded outwardly from the outer tube.

The lead removal apparatus may also be characterized as comprising an outer tube having a passageway extending longitudinally therethrough, which is sized for insertion into the passageway of the coiled structure; an anchoring projection positioned proximal the distal end of the outer tube; and a stylet positioned through the outer tube passageway and urging the anchoring projections between relaxed and hooked positions. In the hooked position, the anchoring projection extends outwardly from the outer tube and when also positioned in the coiled structure passageway hooks into the coiled structure. In the relaxed position, the anchoring projection is insertable into the coiled structure passageway for positioning therein.

The foregoing problems are also solved and a technical advance is achieved with illustrative apparatus for removing an elongated structure such as a catheter or an electrical pacemaker lead implanted in biological tissue such as a blood vessel or a heart cavity wall. The illustrative apparatus includes a control unit having a longitudinal passageway such as a flexible tube that is insertable in the longitudinal passageway of the catheter or the wire coil of the pacemaker lead for controlling movement of the elongated structure. Positioned about the distal end of the control unit is an expandable unit that is operable to a position for securing the control unit to the elongated structure. The control unit passageway is used for operating the expandable unit.

In a first embodiment, the control unit is a flexible tube with one or more side ports or apertures for passing a fluid therethrough for operating the expandable unit. In this embodiment, the expandable unit is a balloon attached about the distal end of the tube with the side ports leading from the passageway for inflating or expanding the balloon to an expanded position for securing the control unit to the elongated structure.

In a second embodiment, the control unit again includes a flexible tube. The expandable unit includes a number of twisted radial projections each having a free end that is formed from radial strips cut in the distal end of the tube. The strips are twisted at the free end and pushed into the passageway of the tube. The apparatus further comprises an actuator such as a rod that is inserted into the passageway of the tube to engage and expand the free end of the projections into the wire coil of the pacemaker lead, thereby securing the control tube to the wire coil.

In a third embodiment, a plurality of expandable strips are longitudinally formed in the distal end of the control tube. The actuating rod of the apparatus is inserted in the tube passageway and attached at the distal end of the tube. When the apparatus is inserted in the passageway of the elongated structure, the actuator rod is pulled in a direction out of the tube while operating the deformable strips into an expanded position engaging the wall of the structure passageway for securing the control tube to the elongated structure.

In a fourth embodiment, a number of barbs or a helical ridge is formed at the end of the control tube. The expandable distal end of the control tube is partially collapsed or formed such that the barbs or ridge when expanded by an actuator rod extend beyond the nominal diameter of the tube. The actuator rod is extended through the tube passageway to expand the distal end of the tube and cause the barbs or ridge to engage the structure and secure the control tube thereto.

In a fifth embodiment, the apparatus also includes a hollow control tube having a longitudinal passageway therein. An expandable slotted sleeve is positioned at the distal end of the control tube. An actuator rod is inserted through the slotted sleeve and control tube. The distal end of the rod is enlarged to engage and expand the slotted sleeve against the distal end of the control tube. When inserted in the passageway of the elongated structure, the actuator rod is pulled in a direction out of the control tube passageway to force the enlarged distal end of the rod into the passageway of the slotted sleeve and expand the slotted sleeve into the wall of the elongated structure. As a result, the control tube is secured to the elongated structure for controlling the movement thereof.

In sixth and seventh illustrative embodiments similar in function to the fifth embodiment, an expandable sleeve comprising a pliable material is positioned between the distal ends of the control tube and actuating rod. In the sixth embodiment, the pliable material sleeve is compressed between the distal ends of the control tube and actuator rod to expand and engage the passageway walls of the elongated structure. In the seventh embodiment, the pliable material sleeve is already in an expanded position to engage the passageway walls of the elongated structure. To insert this expanded pliable material sleeve into the passageway of the elongated structure, the actuator rod is pushed into the passageway of the control tube to longitudinally stretch the pliable material sleeve. As a result, the outside diameter of the sleeve is compressed to allow the apparatus to be inserted into the passageway of the elongated structure. When inserted, the actuator rod is released allowing the sleeve to radially expand and engage the wire coil or passageway walls of the elongated structure.

The invention is further directed to removal apparatus having a guide that is insertable into the passageway of the elongated structure for guiding the control unit in the passageway. In those instances where the passageway of the elongated structure has become blocked or occluded, the apparatus advantageously includes this guide for breaking through the occlusion. Furthermore, various diameter guides are inserted into the structure passageway for determining the minimum passageway diameter of the structure when the structure has in some way been deformed or damaged. Illustratively, the guide includes a stylet wire that is first inserted into the passageway of the elongated structure. When the stylet guide has been inserted, the control tube is inserted over the proximal end of the stylet wire and inserted into the passageway of the structure. In one embodiment, the expandable unit of the apparatus includes a wire coil positioned around and attached at its distal end to the control tube. When inserted, the control tube is rotated to expand the wire coil and secure the control tube to the elongated structure.

In another embodiment, the expandable unit includes a balloon attached about the distal end of the control tube. The control tube includes a second passageway that leads to the balloon for inflating the balloon to secure the control tube to the passageway wall of the elongated structure.

The invention is also directed to a removal apparatus having a rotatable unit for securing the control unit to the elongated structure. In one illustrative embodiment, the removal apparatus includes a control tube insertable into the passageway of the elongated structure for controlling the movement thereof. Positioned about the distal end of the control tube is a rotatable unit such as a cylindrical rod that is rotatable to a position off-centered from the tube for securing the control tube to the elongated structure. The apparatus also includes an actuator rod extending through the control tube and attached off-centered to the cylindrical rod for rotating the rod into the off-centered position securing the control tube to the structure.

The invention is still further directed to removal apparatus having a control tube that is insertable into the passageway of the elongated structure and has an extended projection at the distal end thereof for securing the tube to the structure. Also included is a stylet that is insertable into the passageway of the tube for operating the extended projection to a retracted position for insertion or removal of the control tube from the passageway of the elongated structure.

The invention also includes apparatus for separating the elongated structure from tissue that is restricting the movement and, consequently, the removal of the elongated structure. In one illustrative embodiment, the separating apparatus includes a tube having a first passageway for receiving the elongated structure. Positioned about the distal end of the tube is a balloon that is inflatable for separating restricting tissue from a length of the elongated structure. A second passageway extending along the tube and to the balloon is included for inflating the balloon.

In another embodiment, the separating apparatus includes a first tube having a passageway for receiving the elongated structure and a distal end for separating the structure from the restricting tissue as the elongated structure is received into the passageway. Also included is a second tube having a passageway for receiving the elongated structure and the first tube for separating the restricting tissue from either the first tube or the elongated structure. Advantageously, at least one of the two tubes comprises a polypropylene material, which is much less susceptible to kinking than teflon. In operation, two tubes are alternately moved along the elongated structure to provide tissue separation. The second tube advantageously adding strength to the removal apparatus for separating the restricting tissue. A control mechanism having a passageway for passing the proximal end of the elongated structure therethrough is also attached to the proximal end of the first tube for controlling movement of the first tube in either a rotational or longitudinal direction about the elongated structure. To facilitate visualization of the separating apparatus in biological tissue such as a blood vessel, at least one of the two tubes includes a radio-opaque material such as bismuth.

The invention also includes apparatus for separating the distal end of an elongated structure such as a pacemaker lead from heart tissue affixed thereto. In one illustrative embodiment, the separating apparatus includes first and second concentric tubes each having a passageway for receiving the structure to the distal end thereof. An elongated member such as stainless steel wire or suture material is extendable between the distal ends for cutting the distal end of the structure from the tissue. When the tubes are positioned at the distal end of the coiled structure, the tubes are rotated in opposite directions to wipe the wire or suture material across the distal ends of the tubes and structure, thereby cutting the distal end of the structure from the affixed tissue. At least one of the tubes also has a second passageway or channel for controlling the amount and the tension of the elongated means at the distal ends thereof.

In a second illustrative embodiment, the separating apparatus includes a tube having a passageway for receiving the lead. The distal end of the tube is extendable to the distal end of the pacemaker lead. Included at the distal end of the tube is a plurality of slots for receiving the tines of the pacemaker lead. When the tines have been positioned in one or more of the slots, the tube is rotated for separating the tines and distal end of the lead from the encapsulating tissue.

The invention is further directed to apparatus for expanding the proximal end of a severed coiled structure of a pacemaker lead. Advantageously, this expands the wire coil structure of a pacemaker lead to insert a sizing stylet or gauge to accurately determine the diameter of the wire coil of the pacemaker lead. When the connector end is severed from the proximal end of the pacemaker lead, the severing operation deforms the wire coil and provides a false indication of the true diameter of the passageway extending to the distal end of the lead. The expanding apparatus includes a tapered rod having distal end with a first diameter that is easily insertable into a passageway of the coiled structure of the pacemaker lead. The rod has a tapered longitudinal portion extending from the distal end to a proximal end having a second diameter greater than the first diameter. The tapered portion engages and expands the proximal end of the severed coiled structure when inserted therein. The apparatus also includes a control mechanism attached to the rod for controlling movement of the rod in the passageway of the coiled structure.

The invention includes apparatus for removing an elongated coiled structure implanted in biological tissue such as the wire coil of a pacemaker lead implanted in the heart through a blood vessel leading thereto. The apparatus includes a stylet wire that is insertable into a longitudinal passageway of the coiled structure for controlling movement of the structure. A wire coil is attached at its distal end to the distal end of the stylet wire and is expandable for securing the stylet wire to the coiled structure. The proximal end of the wire coil is extended from the wire coil and stylet wire for engaging the coiled structure and for controlling expansion of the wire coil.

In another illustrative embodiment of this removal apparatus, first and second coil means, such as a wire coil having respective first and second pluralities of turns, are positioned about the distal end of the stylet wire. The first coil means is attached about the distal end of the stylet wire and is radially expandable about the stylet wire for securing the stylet wire to the implanted lead when the stylet wire is inserted in the longitudinal passageway of the implanted lead. The second coil means extends proximally from the first coil means and laterally from the stylet wire for advantageously engaging the implanted lead and radially expanding the first coil means about the stylet wire. The second plurality of wire turns is formed to have a predetermined length and width for advantageously engaging the coil structure of the implanted lead. Furthermore, the second plurality of wire turns and stylet wire cooperatively have a cross-sectional dimension approximating that of the implanted lead passageway. The first coil means also includes a third plurality of closely-spaced wire turns that extends distally from the first plurality and that is positioned around and attached to the stylet wire. The second and third pluralities of wire turns cooperate to radially expand the first plurality of wire turns. An enhancement to this illustrative embodiment includes a flat and a tapered portion of the stylet wire that is positioned between the first and third pluralities of wire turns for unremovably engaging the coiled structure of the implanted lead. The width of this flat portion approximates the width of the implanted lead passageway. The tapered portion extends proximally from the flat portion for advantageously expanding the first plurality of wire turns within the passageway of the implanted lead. The tapered portion more quickly expands the first plurality of wire turns to engage the coiled structure of the implanted lead and secure it thereto without retraction of the stylet wire from the electrode of the implanted lead. In addition, the distal end of the stylet wire is tapered for easy insertion into the implanted lead passageway.

In another embodiment of the lead removal apparatus of the present invention, the lead removal apparatus preferably includes a tube, and control means for moving the coiled structure of a cardiac lead when secured to the coiled structure. The control means is slidably arranged in the tube and has a distal end that is configured for insertion into the passageway of the coiled structure. The expandable means is other than and separate from the control tube and is positioned proximate the distal end of the control means. The expandable means has an expanded position in the passageway of the coiled structure for securing the control means to the coiled structure such that there is a more secure lock or engagement with the coiled structure and there are advantageously fewer failures in the locking engagement, thereby providing a more reliable mechanical connection. This particular arrangement also further provides greater size tolerance when selecting an appropriate lead removal apparatus and advantageously provides a wider range of lead passageway sizes for a given stylet diameter. This configuration also provides for less dependence on physician technique and experience than the previously described coiled structure.

The expandable means of the lead removal apparatus advantageously includes a laterally flexible member that extends longitudinally and proximally from the distal end of the control means. The laterally flexible member advantageously thus has a proximal end for assuming an expanded position and engaging the turns of a coiled structure. The laterally flexible member is attached to the distal end of the control means and is further secured thereto with a sleeve positioned around the laterally flexible member and control means. In one embodiment, the control means comprises a stylet with the laterally flexible member including a folded-back portion or a plurality of folded-back portions of the stylet.

To facilitate fixing the relative positions of the stylet and outer tube, a lock is positioned at the proximal ends of the tube and stylet. For operation of the lead removal apparatus, handles are positioned proximate the proximal ends of the control tube and stylet.

In another aspect of the invention, the lead removal apparatus that includes a locking stylet and a radially expandable portion that comprises a plurality of expandable members. A actuator portion, such as a elongate cannula or section or coiled wire, is advanced against the expandable portion, causing the latter to expand radially and engage the coils of the pacemaker lead into which it has been introduced. In one embodiment, the expandable portion comprises a wrap of multifilar wires (six to a bundle) that is helically wound around the distal portion of a stylet pull wire. The multifilar bundle is soldered together and also to the distal end of the stylet such that the expandable portion is longitudinally compressible. When compressed, the expandable members bow outward and form an irregular shaped, tangled mass that presses outward against, and between the coils to provide positive engagement for subsequent retraction of the pacemaker lead. To prevent premature advancement of the actuator portion and expansion of the expandable member, an optional deployment guard, such as a severable ligature, can secure the actuator portion and stylet together, generally via their respective handles.

In another embodiment of the invention, the expandable portion comprises a series of longitudinally parallel wires that expand outward when deployed. In still another embodiment, the expandable portion comprises a slotted cannula in which the expandable members between the longitudinal slots bow outward to engage the coils of the pacemaker lead.

The foregoing problems are solved and a technical advance is achieved in a lead apparatus, wherein the handle of the lead removal apparatus includes a proximal portion of the handle of a lead removal apparatus which is formed into a pre-shaped first configuration, such as a series of coiled loops. The coiled loops provide the operator with a greater ability to apply traction on the locking stylet and pacemaker lead and helping to maintain the proximal portion of the apparatus within the sterile field. The proximal portion can constrained into a second, sufficiently straight configuration that allows the operator to feed a medical device, such as a dilator sheath thereover, such as for disrupting scar tissue encasing the lead along the path of the vein.

BRIEF DESCRIPTION OF THE DRAWINGS

FIG. 3 illustrates sections of the apparatus of the present invention for separating a length of a heart lead restricted in a blood vessel and for separating the tip of the heart lead from a heart cavity wall;

FIG. 4 illustrates the leading edge of the separator tube of the apparatus of FIG. 3 for separating the heart lead from a blood vessel as partially shown in FIG. 1;

FIGS. 24–26 depict illustrative apparatus for separating the distal end of an elongated structure from tissue affixed thereto;

FIG. 28 depicts an alternative embodiment of the apparatus for removing an elongated coiled structure implanted in biological tissue; and FIGS. 29–31 depict an enhancement to the alternative embodiment of the apparatus for removing an elongated coiled structure implanted in biological tissue of FIG. 28.

FIGS. 32 and 33 depict an alternative embodiment of the lead removal apparatus of the present invention;

FIG. 37 depicts an alternative embodiment of the expandable unit of the lead removal apparatus of FIG. 32;

FIG. 38 depicts an enlarged, cross-sectional view of the expandable unit of FIG. 37 taken along the line 38—38; and FIG. 39 depicts a partially sectioned side view of the control tube and stylet of the lead removal apparatus of FIG. 33.

FIG. 40 depicts a partially sectioned side view of an alternative embodiment of the present invention having a multifilar, helical expandable portion;

FIG. 41 depicts a method of forming the expandable portion of the embodiment of FIG. 40;

FIG. 42 depicts a side view of an embodiment of the present invention having a expandable portion with longitudinally parallel elements;

FIG. 42A depicts a cross-sectional view taken along line 42A—42A of FIG. 42;

FIG. 43 depicts a side view of an embodiment of the present invention wherein the expandable portion comprises a slotted cannula;

FIG. 43A depicts a cross-sectional view taken along line 43A—43A of FIG. 43;

FIGS. 44–45 depicts a sectioned view of the embodiment of FIG. 40 being deployed inside the coil of a pacemaker lead;

FIG. 46 depicts a side view of an embodiment of present invention in which the proximal portion of the handle includes a compacted shape.

DETAILED DESCRIPTION

Figure 1:
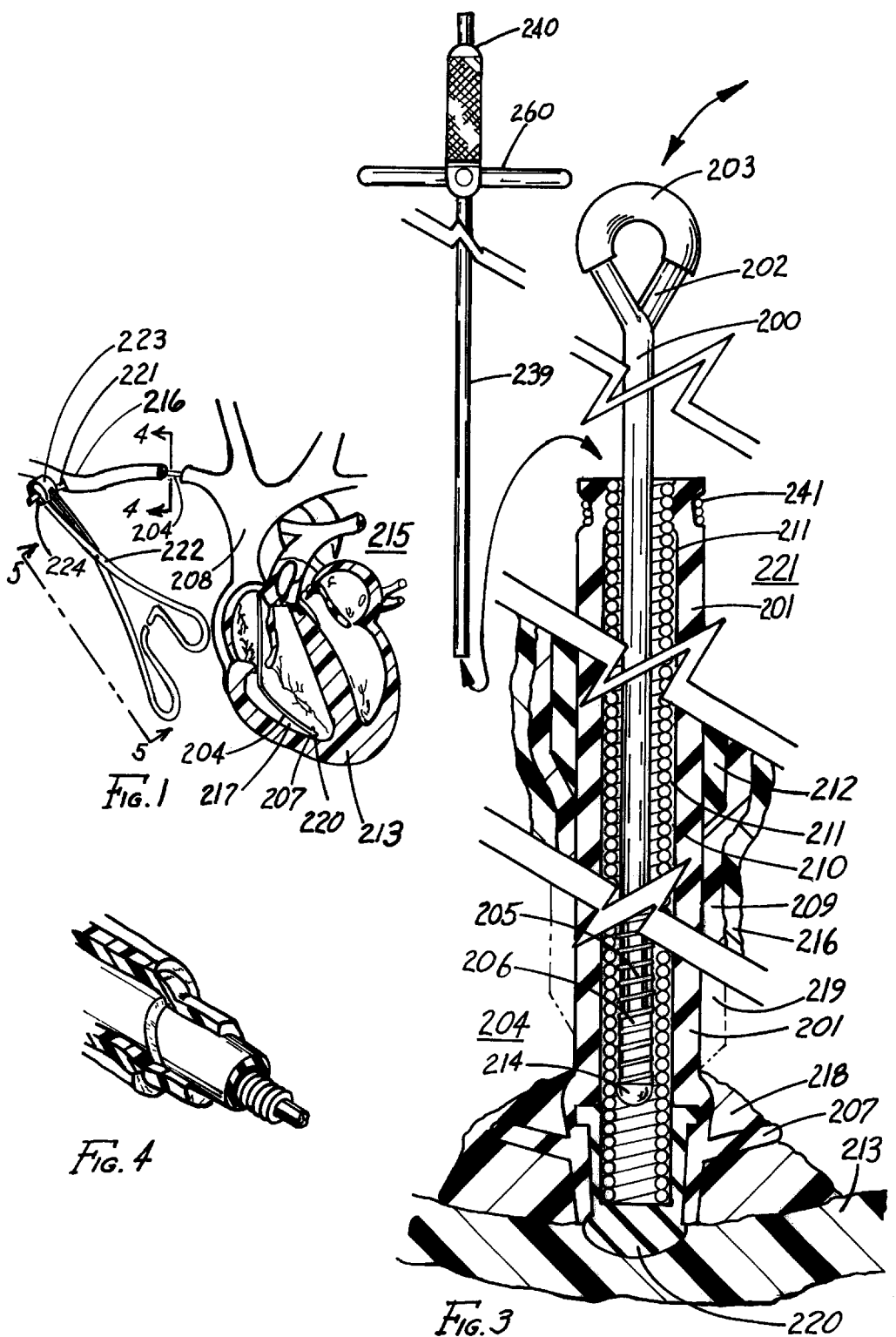
FIG. 1 depicts a partial cross-sectional view of a heart having an electrical pacemaker lead implanted therein.

Depicted in FIG. 1 is a partial cross-sectional view of heart 215 connected to a plurality of arteries and veins such as the right subclavian vein 216 through which an electrical heart pacemaker lead 204 has been implanted. The lead passes internally through the right subclavian vein 216, the superior vena cava 208 and into the right ventricle 217 of the heart. The distal end of the lead includes an electrode 220 for electrically stimulating the heart and is secured to the apex of the right ventricle with a plurality of tines 207, which in time become securely attached to the ventricle wall by endothelial tissue forming around the heart lead tip. Some ventricles are relatively smooth on the inside, but most have trabeculae amongst which the tines are secured into position. External to the right subclavian vein, the proximal end 221 of the lead is grasped by a lockable mechanism 222, which will be described hereinafter.

Figure 2:
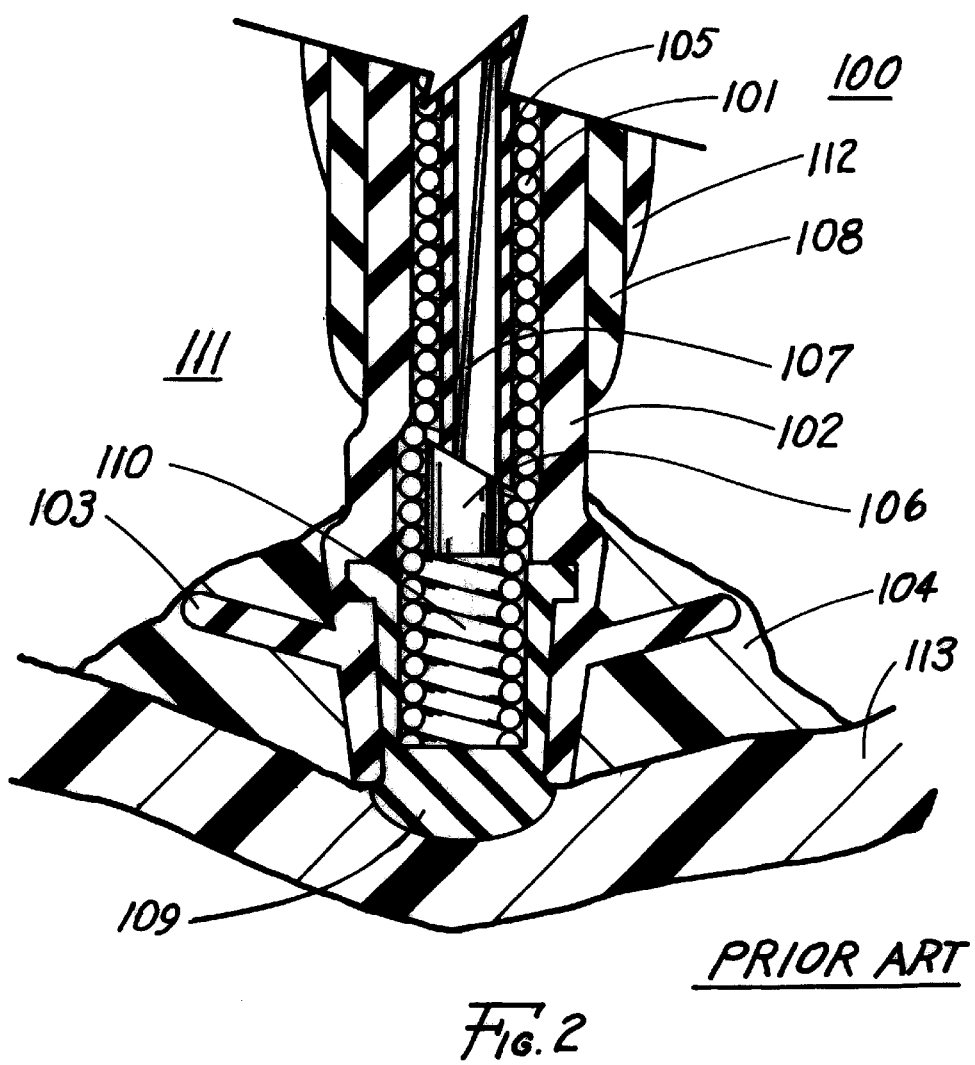
FIG. 2 depicts a partial cross-sectional view of a prior art tool inserted in the passageway of a heart lead for removing the lead.

Depicted in FIG. 2 is a partial cross-sectional view of a prior art tool 100 for removing a heart lead 111 which has been secured to a heart cavity wall 113 via trabeculae and/or fibrotic tissue 104. The lead includes an electrical coiled structure 101 and insulating material 102 that is formed essentially into a tube for covering the outer surface of the coiled structure and for preventing fluids from entering the coiled structure. At the distal end of the heart lead are tines 103, that are formed from the insulating material, for securing the heart lead tip including electrode 109 to the heart cavity wall. Tool 100 includes a hollow rigid tube 105 and beveled rod 106 for inserting in the longitudinal passageway 110 of the heart lead coiled structure. In the passageway of hollow tube 105 is an actuating wire 107 connected to beveled rod 106. The trailing edge of the beveled rod and the leading edge of the hollow tube are inclined at an angle for moving the beveled rod across the distal end of the hollow tube when the actuating wire is pulled. When moved, the beveled rod engages and deforms the heart lead coiled structure as shown. The deformed coiled structure locks the hollow tube and beveled rod in place for limiting movement of the heart lead.

However, once secured, beveled rod 106 may not be extracted from passageway 110 of the coiled structure since the deformed coiled structure prevents the beveled rod and actuating wire from traversing the passageway. The prior art tool also includes a hollow dilator 108 for sliding over the heart lead coil and separating the heart lead from the blood vessel. A hollow explanator 112 passes over the dilator and is rotated back and forth to explant the tip of the heart lead from the securing tissue and heart wall.

Depicted in FIG. 3 is a flexible stylet wire 200 of the present lead removal apparatus invention that is insertable in the longitudinal passageway 210 of a heart lead coiled structure 211 for controlling and, in particular, limiting the movement of heart lead 204 including coiled structure 211. Heart lead 204 also includes insulating material 201, such as silicone or polyurethane, formed into a hollow tube that surrounds the coiled structure and prevents fluids from making contact with the coiled structure. Attached to the distal end of the flexible stylet wire is an expandable wire coil 205 consisting of approximately 25 turns of wire with spacing between the turns. Five to seven wraps of the wire coil are attached to the distal end of the stylet wire using, for example, solder 206. The remaining wraps of the wire coil remain free for engaging the coiled structure when the proximal end of the stylet wire is rotated in a direction to unwind and expand the turns of the wire coil and engage the coiled structure of the heart lead. A bead 214 of high temperature silver solder is applied to the distal end of the stylet wire to prevent the distal end thereof from pulling through the wire coil during separation and removal of the heart lead. Positioned about the proximal end of the stylet wire is control mechanism 202 for rotating the stylet wire in either a clockwise or counterclockwise direction or for moving the wire in a longitudinal direction into or out of the passageway. In this embodiment, control mechanism 202 is a loop of wire formed from the stylet wire of which the physician may grasp or insert his finger. The loop may also be fashioned for attachment to another control mechanism for moving the stylet wire. Other control mechanisms such as a slidable chuck may be positioned at the proximal end of the stylet wire to facilitate movement of the stylet wire. The formed loop 202 is covered with teflon tubing 203 or other suitable material for facilitating the easy movement of the stylet wire. The looped end is also compressible for inserting through a separator tube 212.

Figure 5:
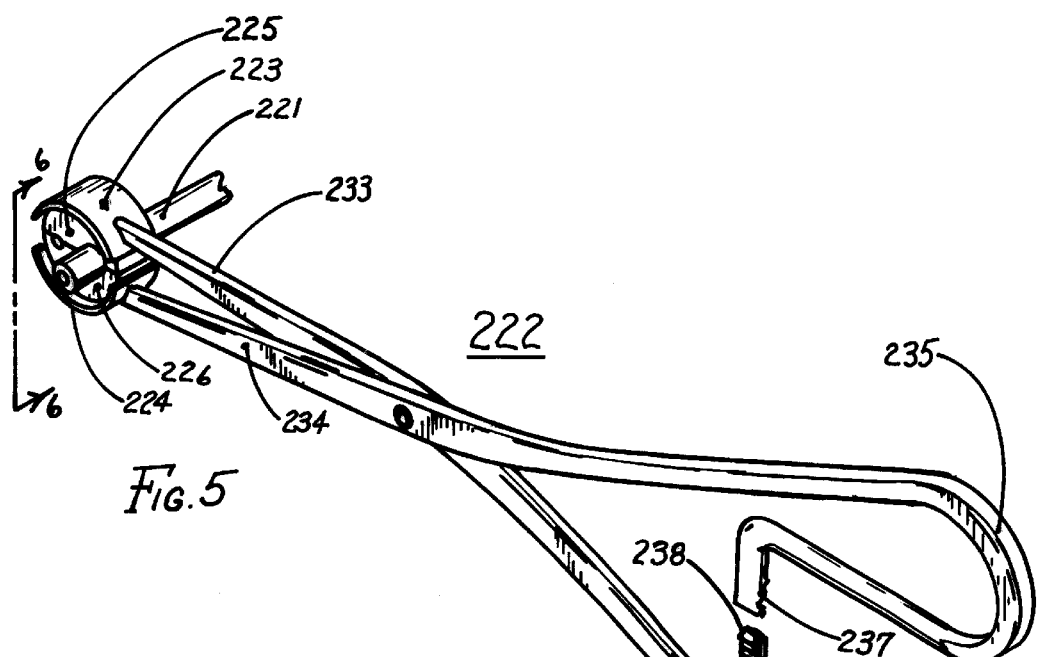
FIG. 5 depicts a lockable mechanism for grasping the proximal end of the pacemaker lead of FIG. 1.
Figure 6:
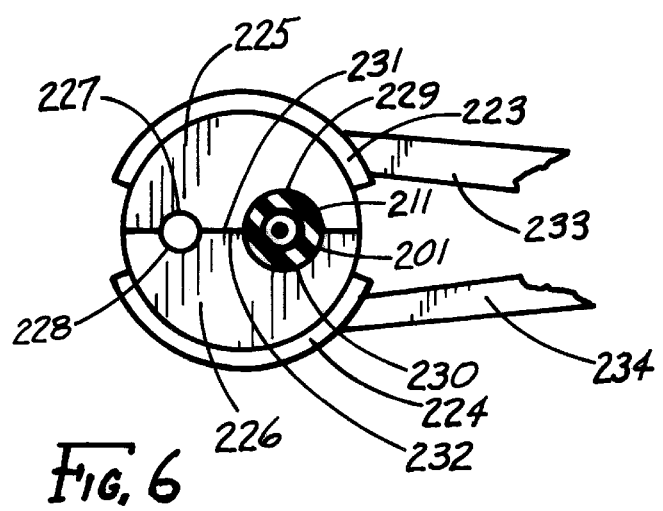
FIG. 6 depicts an enlarged view of the lockable mechanism of FIG. 5 along the lines 6—6.

The choice of the stylet wire and wire coil varies with the internal diameter of the coiled structure which varies from 0.016" to about 0.028" for most heart leads. The diameter of the stylet wire would then range from 0.009" to 0.015", with the coil wire ranging in diameter from 0.003" to 0.006". The use of stainless steel wire is preferable. The stylet wire should be hardened wire, but ductable wire may be used for the coil wire. Before the stylet wire is inserted into passageway 210 of the lead, the inside diameter of the coiled structure and the outside diameter of the insulating material are determined. First, lockable mechanism 222 is first applied to the proximal end 221 of the lead between opposing semicircular jaws 223 and 224. The details of mechanism 222 are depicted in FIGS. 5 and 6. Semicylindrical pliable material 225 and 226, such as latex, are affixed with medical grade adhesive to the opposing faces of the jaws. Semicylindrical pliable material 225 includes semicylindrical channels 227 and 229 having different radii, and pliable material 226 includes semicylindrical channels 228 and 230 with radii corresponding to channels 227 and 229, respectively. When jaws 223 and 224 are in a closed position, the opposing surfaces 231 and 232 of respective pliable material 225 and 226 are in contact with opposing channels 227 and 228 forming one hollow cylindrical passageway with a first diameter and opposing channels 229 and 230 forming a second hollow cylindrical passageway with a second larger diameter. The two different size diameter passageways in the pliable material accommodate a number of different size diameter pacemaker leads and are designed to grasp and apply pressure to insulating material 201 in a uniform manner.

When proximal end 221 of lead 204 is inserted and grasped in the hollow passageway formed by channels 229 and 230, insulating material 201 is compressed onto coiled structure 211, thus limiting the movement of the structure within the insulating material. When the physician cuts the lead for access to the passageway of the lead, the compressed insulating material prevents the coiled structure from retracting into the passageway of the lead.

Pivotally interconnected elongated members 233 and 234 are connected to respective opposing jaws 223 and 224 to operate the jaws between open and closed positions. The proximal ends 235 and 236 of the members are curved as shown in FIG. 5 to oppose each other and have a respective plurality of teeth 237 and 238 that interlock to form a locking mechanism. The locking mechanism is actuated by squeezing the proximal ends of the members and opposingly positioning the teeth thereon. When so positioned, the teeth of mechanism 222 interlock and maintain opposing jaws 223 and 224 in a closed position.

After the lockable mechanism is applied to the proximal end of the pacemaker lead, a pair of well-known wire cutters or snips sever the electrical connector (not shown) from the proximal end 222 of pacemaker lead 204. As a result of such severance, coiled structure 211 of the pacemaker lead is commonly deformed, thereby presenting a false indication of the actual diameter of longitudinal passageway 210. As a consequence, the physician inserts expansion device 901 into the proximal end of hollow passageway 210 to expand coiled structure 211.

Figure 9:
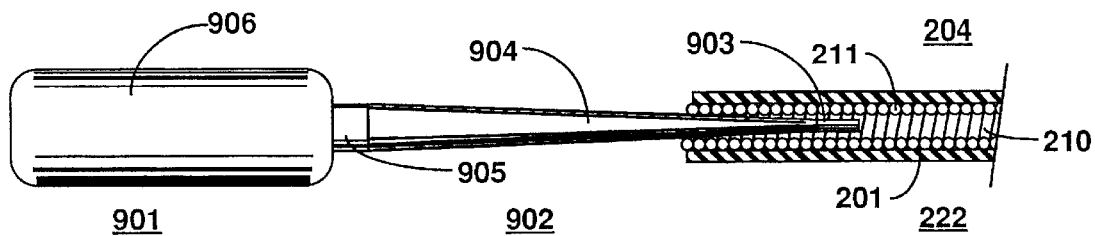
FIG. 9 depicts a device for expanding the proximal end of the coiled structure of FIG. 3.

Depicted in FIG. 9 is expansion device 901 for expanding the deformed proximal end of coiled structure 211. The expansion device includes a tapered rod 902 having a distal end 903 with a diameter that is easily insertable into the passageway of the deformed coiled structure. Tapered rod 902 includes a tapered longitudinal portion 904 that gradually increases in diameter to proximal end 905 that has a diameter significantly greater than the diameter of the distal end. Control handle 906 is connected to the proximal end of the tapered rod. The physician grasps the control handle to insert the tapered rod into the longitudinal passageway and to expand the deformed proximal end of the coiled structure.

With lockable mechanism 222 in a closed position and the proximal end of the coiled structure expanded, the physician selects a wire guide 239, as shown in FIG. 3, having a diameter less than the diameter of the lead passageway. The physician determines the passageway by inserting the wire guide therein and sensing for any blockages. The guide includes a control mechanism such as a knurled cylindrical chuck 240 positionable about the proximal end thereof. The physician grasps the knob to extend the guide into the lead passageway and to rotate the guide back and forth to clear or break through any blockages caused by tissue or occluding material. The guide is also used to determine or size the inside diameter of a second coiled structure that may be coaxially positioned inside coiled structure 211. When utilized as a control mechanism for stylet wire 200, the chuck may also include appendages 260 for rotating and counting the number of times the stylet wire is rotated. Having determined the lead passageway with the wire guide, several other guides similar to guide 239 are individually inserted in the passageway to determine the actual inside diameter at the proximal end. Guide 239 is also utilized to determine if coiled structure 211 has been deformed or damaged and to determine the smallest diameter of the coiled structure and passageway.

As shown in FIG. 3, stylet wire 200 is inserted into longitudinal passageway 210 of coiled structure 211. The diameter of the coil wire and stylet wire have been selected to form a combined overall diameter which approximates the diameter of the longitudinal passageway of the heart lead coiled structure within a predetermined tolerance such as one or two thousandths of an inch. Stylet wire 200 is then fed through the entire length of the passageway to the distal end of the coiled structure which is secured to the wall of heart cavity tissue 213 via tines 207. When fully inserted into the heart lead, the distal ends of the stylet wire and coiled structure should be in close proximity. It is not necessary, but probably more advantageous, that the stylet wire be attached to the distal end of the heart lead. For separating the heart lead from adjacent tissue, the stylet wire may be secured anywhere along the passageway of the coiled structure past the restricting tissue. To secure the stylet wire to coiled structure 211, looped end 202 of the stylet wire is operated in a circular direction to unwind and expand wire coil 205. As a result, the turns of the wire coil and coiled structure engage and intermesh, thereby firmly securing the stylet wire to the heart lead. This prevents any extension or stretching of the heart lead and also controls and limits the movement of the lead when separator tube 212 is moved along the length of coiled structure 211 and insulating material 201 of the heart lead.

Figure 23:
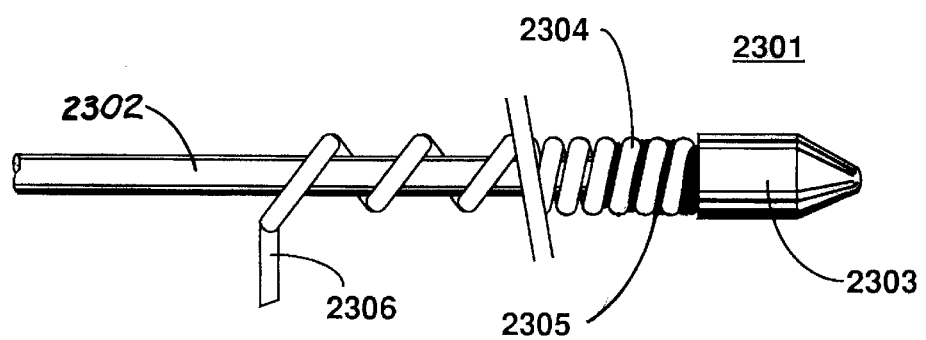
FIG. 23 depicts an alternative embodiment of the apparatus for removing an elongated coiled structure implanted in biological tissue of FIG. 3.

Depicted in FIG. 23 is illustrative removal apparatus 2301, which is an alternative embodiment of stylet wire 200. Removal apparatus 2301 is insertable into the longitudinal passageway of an elongated structure such as a pacemaker lead. The removal apparatus includes a stylet wire 2302 with a conically-shaped silver solder tip 2303 that is positioned at the distal end thereof. Closely wrapped wire coil 2304, similar to wire coil 205, is attached at the distal end of the stylet wire using silver solder 2305 as previously described. The proximal end of the wire coil is pulled to unwrap several turns of wire coil 2304. A pigtail 2306 is formed from the proximal end of the wire coil to extend in a radial direction from the wire coil and stylet wire. Pigtail 2306 catches on or engages the coiled structure of the pacemaker lead to engage wire coil 2304 with the coiled structure of the pacemaker lead. In addition, the wire coil may be rotated in the opposite direction to release the stylet wire from the coiled structure if desired.

Depicted in FIG. 28 is illustrative removal apparatus 2801, which is an alternative embodiment of stylet wire 200. Removal apparatus 2801 is insertable into the longitudinal passageway of an elongated structure such as a pacemaker lead. The removal apparatus includes stylet wire 2802 comprising commercially available stainless steel wire approximately 0.021" in diameter and 61 cm in length. Stylet wire 2801 has distal end 2803 which is tapered into a conical shape for an approximate length of 4 cm for easy insertion into the pacemaker lead passageway. Tapered distal end 2803 is shaped using any of a number of well-known techniques such as sanding, grinding, buffing, or a combination thereof. The removal apparatus also includes wire coil 2804 comprising commercially available Tophel wire approximately 0.0045" in diameter. Wire coil 2804 is positioned around and about stylet wire 2802 and comprises central plurality of wire turns 2805. Central plurality 2805 extends longitudinally from approximately 20 cm and comprises wire turns with a spacing of approximately 0.035" therebetween. Wire coil 2804 further comprises a proximal plurality of wire turns 2806, which extends proximally from the central plurality and laterally from the stylet wire, and a distal plurality of wire turns 2807, which extends distally from the central plurality. Proximal plurality of wire turns 2806 has a nominal outside diameter of 0.010" and a maximum diameter width of 0.012". The proximal plurality is formed from turns having an 0.010" inside diameter that are stretched to an outside diameter of approximately 0.010", thus increasing the spacing between each turn. The length of the proximal plurality is trimmed to a length of approximately 12 mm. When inserted in the lead passageway, the stylet wire and proximal plurality in combination have a cross-sectional dimension that approximates that of the passageway for engaging the coiled structure of the lead and radially expanding the central plurality of wire turns. The distal plurality comprises approximately five turns with minimal spacing therebetween, much less than that of central plurality 2805. The distal plurality of wire turns is wrapped about the distal end of the stylet wire next to silver solder bead 2808 and attached thereto with tin-silver solder 2809. The silver solder bead and distal plurality of wire turns are tapered into a conical shape having a maximum outside diameter of, for example, 0.030" for easy insertion in the passageway of the lead.

When apparatus 2801 is positioned in the passageway of an implanted pacemaker lead, in particular a lead having a 0.030" diameter passageway, the proximal plurality of wire turns creates an interference fit in the passageway. During insertion to distal end of the pacemaker lead, the apparatus is alternately pushed distally and pulled proximally a short distance for maintaining the interference fit effected by the engagement of the proximal plurality with the coiled structure of the pacemaker lead. When the distal end of the stylet is positioned in the passageway of the distal end of the pacemaker lead, stylet wire 2801 is rotated in a counter-clockwise direction for unwrapping several turns of central plurality 2805. The unwrapped turns of the central plurality further engage and secure the wire coil of the apparatus with the coiled structure of the pacemaker lead.

Depicted in FIGS. 29 and 30 is illustrative removal apparatus 2901, which represents an enhancement to apparatus 2801 of FIG. 28. Removal apparatus 2901 includes stylet wire 2902 of commercially available 0.021" diameter stainless steel wire having tapered portion 2903, flat portion 2904, and distal end 2905. Removal apparatus 2901 further includes wire coil 2906 having a central plurality of wire turns 2907, a distal plurality of wire turns 2909. Wire coil 2906 also includes a somewhat straight portion 2908 extending longitudinally between the central and distal pluralities. Distal plurality 2909 is closely spaced, much less than the central plurality, and fixedly attached with tin-silver solder 2910 about the distal end of the stylet wire next to silver solder bead 2911. As shown in the top view of FIG. 30, tapered portion 2903 and flat portion 2904 of the stylet wire is positioned between the distal and central pluralities of wire turns and has a maximum width of 0.030' that approximates the width of the passageway of the implanted lead. Straight portion 2908 of the wire coil extends longitudinally from the central plurality along stylet wire 2902 where the diameter of the stylet wire is uniform. Straight portion 2908 further extends longitudinally along tapered portion 2903, which has a 30 degree tapered edge, and flat portion 2904, which has an edge parallel the stylet wire. Tapered portion 2903 and flat portion 2904 are each approximately 0.15' long.

As depicted in FIG. 31, removal apparatus 2901 is positioned in passageway 3001 and secured to coiled structure 3002 of implanted pacemaker lead 3003. Stylet wire 2902 has been rotated in a counter-clockwise direction to wrap straight coil portion 2908 around tapered stylet portion 2903. The wrapped straight coil portion engages the coiled structure of the lead and secures the stylet wire to the implanted lead. As the straight coil portion is wrapped around the tapered stylet portion, turns of the central plurality move distally to expand and engage the tapered stylet portion and the coiled structure of the implanted lead.

Depicted in FIGS. 10–21 are alternative embodiments of illustrative apparatus for removing the elongated structure implanted in biological tissue. All of these alternative embodiments are for controlling the movement of an elongated structure. The removal apparatus in each of these alternative embodiments includes a control unit that is insertable into the longitudinal passageway of the elongated structure, such as a pacemaker lead, and securable to the structure for controlling the movement thereof. The apparatus also includes an expandable unit positioned about the distal end of the control unit and operable to an expanded position for securing the control unit to the elongated structure. However, the control unit in each of these alternative embodiments commonly, but not in all cases, includes a longitudinal passageway for operating the expandable unit to the expanded position for securing the control unit to the elongated structure.

Figure 10:
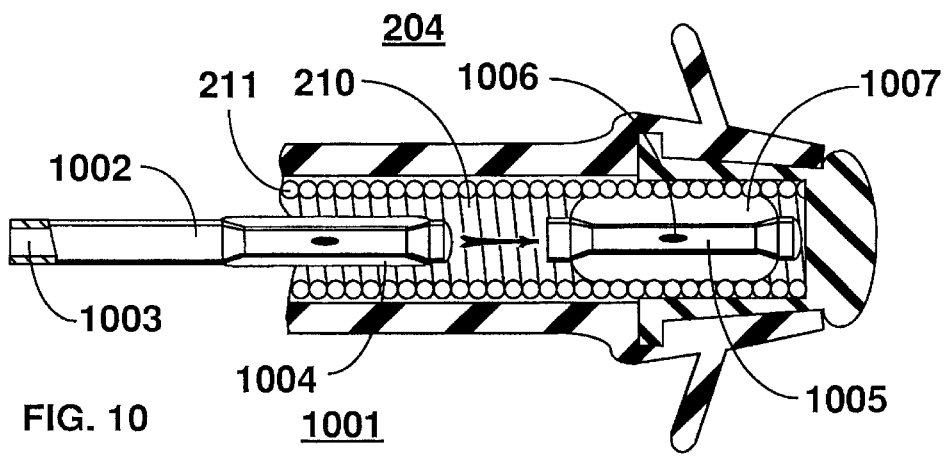
FIGS. 10–21 depict alternative embodiments of the removal apparatus of FIG. 3.

Depicted in FIG. 10 is a first alternative embodiment of illustrative removal apparatus 1001 for removing implanted pacemaker lead 204. The control unit of this removal apparatus includes a flexible tube 1002 having a passageway 1003 formed longitudinally therein. Expandable balloon 1004 is positioned and attached about the distal end of the control tube. The distal end of the control tube is also recessed to attach to the balloon in a well-known manner at the ends of radial recess 1005. The recess also provides a volume in which the collapsed balloon is stored. The recess also includes one or more side ports 1006 leading from passageway 1003 to the balloon. A source of fluid such as compressed air or liquid is passed through the passageway and into the balloon to inflate the balloon to an expanded position as indicated by expanded balloon 1007 positioned at the distal end of the lead.

Figure 11:
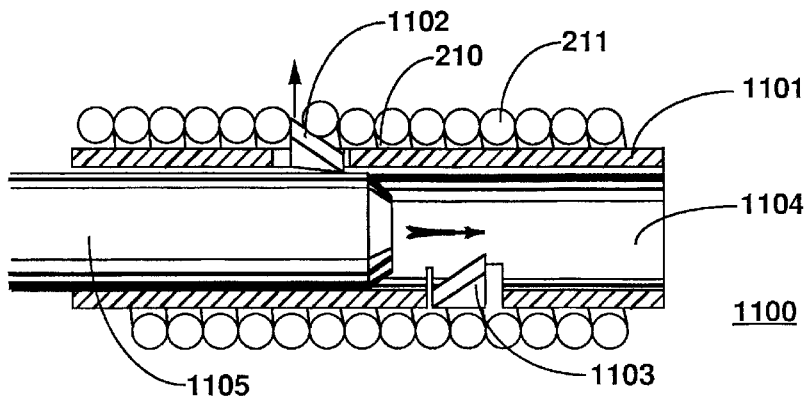

Depicted in FIG. 11 is a second alternative embodiment of illustrative removal apparatus 1100. In this second alternative embodiment, the control unit also includes a control tube 1101 for insertion into passageway 210 of coiled structure 211. The expandable unit comprises a plurality of radial projections 1102 and 1103 that have a free end are radially formed in the distal end of the control tube. The free end of the radial projection is twisted and bent in an inward direction into passageway 1104 of the control tube. As formed, these projections allow a control tube to be easily inserted into passageway 210 of the coiled structure. When control tube 1101 is positioned at the distal end of the coiled structure, actuator rod 1105 is inserted in passageway 1104 of the control tube. When inserted, the actuator rod engages the radial projections and forces them into an expanded position extending radially from the surface of the control tube into the coiled structure of the pacemaker lead. When in the expanded position, these radial projections secure the control tube to the coiled structure, thereby controlling movement of the coiled structure during removal from the tissue.

Figure 12:
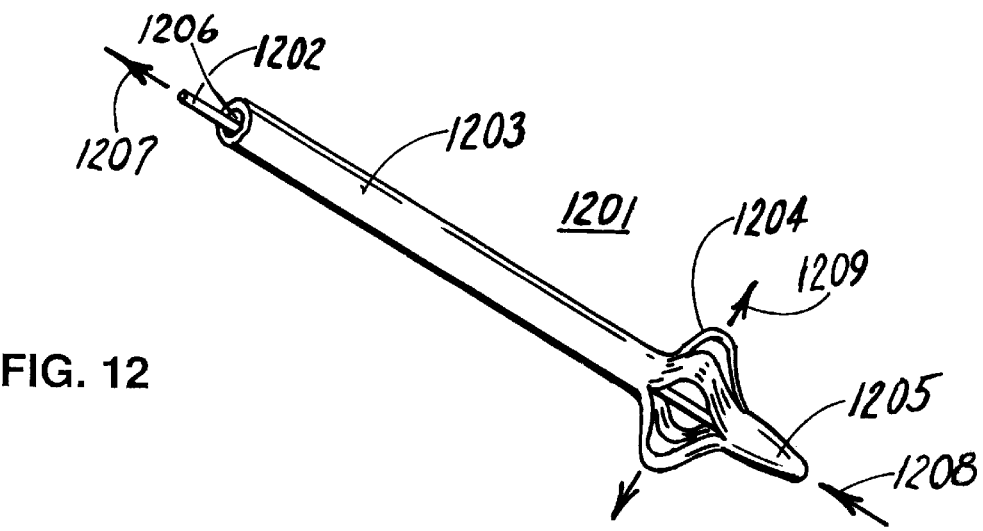

Depicted in FIG. 12 is a third alternative embodiment of illustrative removal apparatus 1201 utilizing an actuator rod 1202. The removal apparatus includes a control tube 1203 that is extendable into the longitudinal passageway of a pacemaker lead. The expandable unit of the apparatus comprises a plurality of longitudinal strips 1204 formed at the distal end of the control tube. Actuator rod 1202 is inserted in the passageway of the control tube and attached to the distal end 1205 thereof. When the control tube is inserted in the longitudinal passageway of the pacemaker lead, the actuator rod 1202 is pulled in a longitudinal direction out of passageway 1206 of the control tube as shown by arrow 1207. Typically, the physician will maintain the relative position of the proximal end of control tube 1203 while the actuator rod is pulled in the outward direction. As a result, distal end 1205 is forced toward the proximal end of the control tube, as shown by arrow 1208, thereby deforming longitudinal strips 1204 in an outward direction as indicated by arrows 1209. The expanding strips engage the coiled structure and secure the control tube to the coiled structure of the pacemaker lead.

Figure 13:
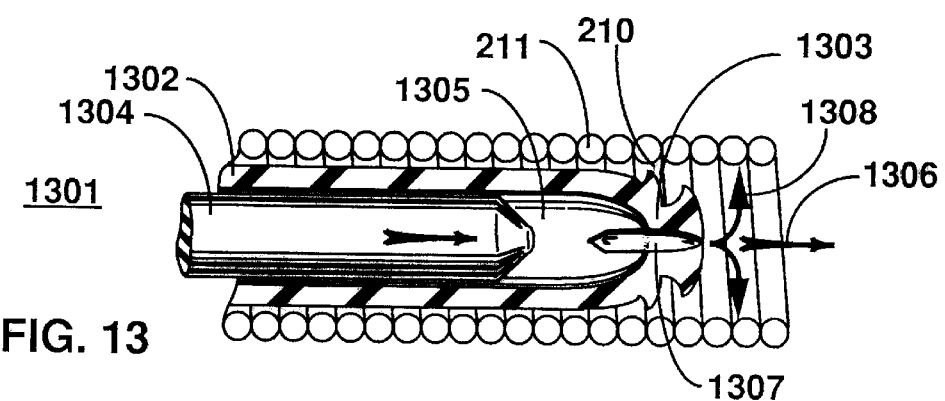

Depicted in FIG. 13 is a fourth embodiment of illustrative removal apparatus 1301 inserted in the longitudinal passageway 210 of coiled structure 211. Removal apparatus 1301 includes a control tube 1302 having a distal end with a spiral or helical ridge 1303 formed therein. Alternatively, a number of barbs are formed in the contoured distal end of control tube 1302. The distal end includes a plurality of slits 1307 or an opening thereat for expanding the ridge or barbs into the coiled structure. Actuator rod 1304 is inserted into passageway 1305 to engage the distal end. When engaged, actuator rod expands the ridge or barbs in a radial direction, as shown by arrows 1308, to engage the coiled structure of the pacemaker lead. As a result, the expanded ridge or barbs secure the control tube to the coiled structure for controlling the movement thereof.

Figure 14:
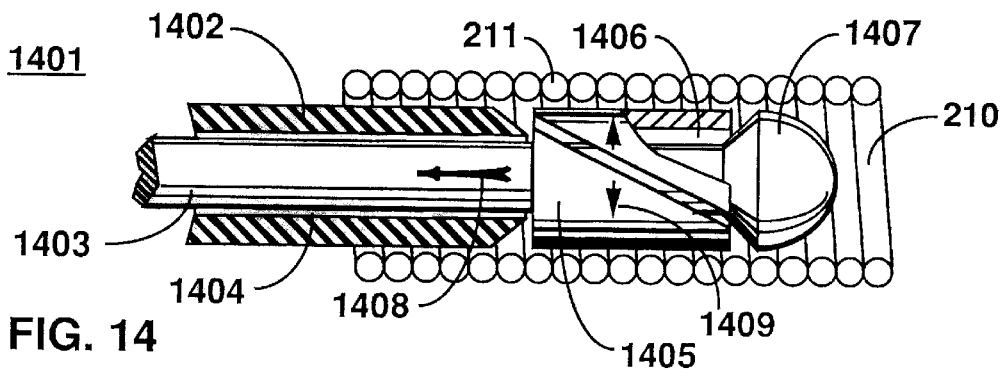

Depicted in FIG. 14 is a fifth embodiment of illustrative removal apparatus 1401 inserted in longitudinal passageway 210 of coiled structure 211. The removal apparatus includes control tube 1402 and actuator rod 1403 extending through hollow passageway 1404 of the control tube. The apparatus also includes a diagonally-slotted sleeve 1405 that is positioned between the distal ends of the control tube and actuator rod. The actuator rod also extends through hollow passageway 1406 of the sleeve. Attached to the distal end of the actuator rod is beveled tip 1407 having an outside diameter approximating the diameter of the control tube and the nominal diameter of the slotted sleeve. Similarly, the distal end of the control tube is beveled to engage and expand the slotted sleeve. To expand the slotted sleeve, the actuator rod is pulled, as indicated by arrow 1408, to engage the sleeve against the beveled edges of the control tube and the rod. As a result, the sleeve is expanded to a position for engaging coiled structure 211 and securing the control tube thereto. The slotted sleeve expands in a radial direction as indicated by arrows 1409.

Figure 15:
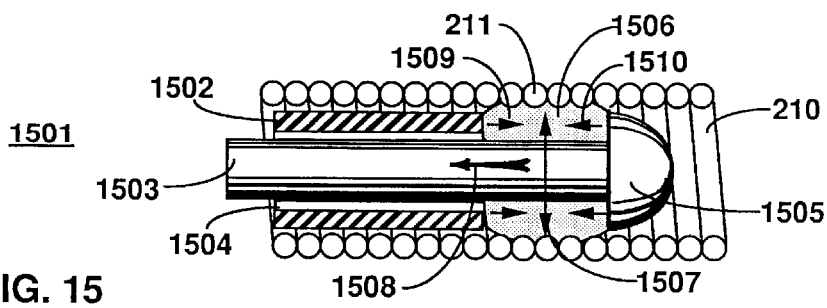
Figure 16:
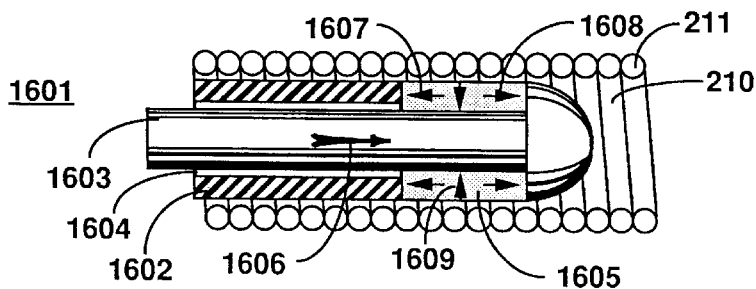

Sixth and seventh alternative embodiments of illustrative removal apparatus 1501 and 1601 are depicted in FIGS. 15 and 16, respectively. In FIG. 15, removal apparatus 1501 includes a control tube 1502 and an actuator rod 1503 extending through longitudinal passageway 1504 of the control tube. The distal end of the actuator rod includes enlarged tip 1505 having a diameter approximating the diameter of the control tube. The device also includes expandable sleeve 1506 comprising a pliable material such as synthetic rubber and the like which expands in a radial direction when compressed between the distal end of the control tube and the enlarged tip of the actuator rod. In the relaxed state, the outside diameter of the pliable material approximates that of the control tube and enlarged tip of the actuator rod for insertion into longitudinal passageway 210 of the coiled structure. When inserted into passageway 210, the enlarged tip and distal end of the control tube compress and radially expand the pliable material in an outward direction toward the coiled structure as indicated by arrows 1507. The actuator rod is pulled through the passageway of the control tube as indicated by arrow 1508. As a result, pliable material 1506 is longitudinally compressed as shown by arrows 1509 and 1510. However, pliable material 1506 also expands in a radial direction and engages the coiled structure, thereby securing the control tube thereto.

Similarly, illustrative removal apparatus 1601 depicted in FIG. 16 includes control tube 1602 having longitudinal passageway 1610, actuator rod 1603 having an enlarged distal tip 1604, and pliable material 1605 attached to the distal end of control tube 1602 and enlarged actuator rod tip 1604. However, unlike pliable material 1506, pliable material 1605 in a relaxed condition has an outside diameter greater than the diameter of longitudinal passageway 210. Therefore, to insert the removal apparatus in the passageway, actuator rod is forced into passageway 1610 as indicated by arrow 1606, thereby stretching pliable material 1605 as indicated by arrows 1607 and 1608. As a result, the outside diameter of the pliable material decreases as indicated by arrows 1609 for insertion into the passageway of the elongated structure. When inserted, the actuator rod is released, and the pliable material attempts to return to its relaxed state. As a result, the pliable material engages the coiled structure and secures the device to the pacemaker lead.

Figure 17:
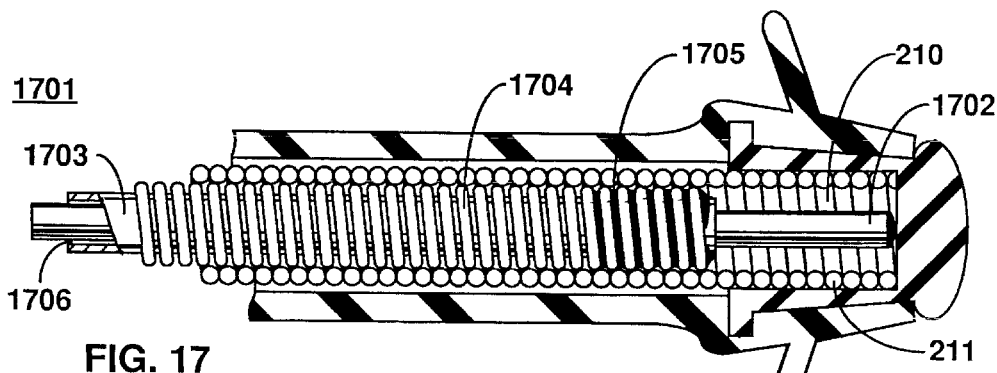
Figure 18:
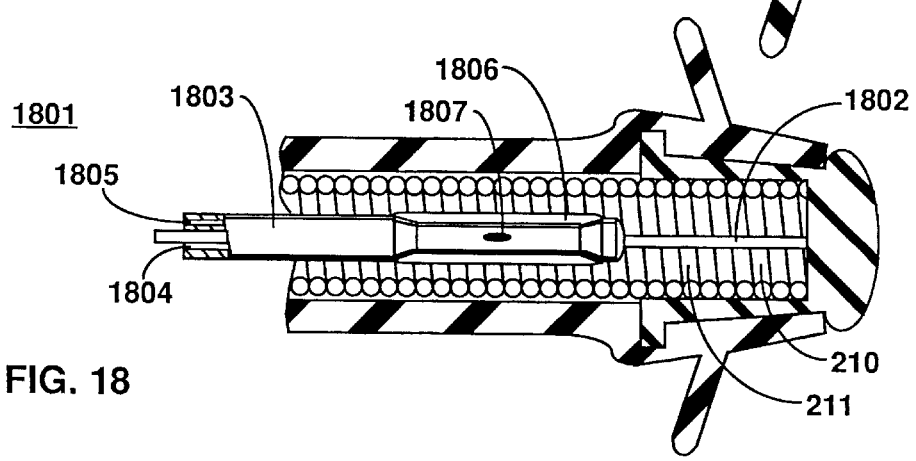

Depicted in FIGS. 17 and 18 are alternative embodiments of illustrative removal devices 1701 and 1801 that include a wire guide for inserting into the longitudinal passageway of the elongated structure. In FIG. 17, removal apparatus 1701 includes wire guide 1702 that is inserted into passageway 210 of coiled structure 211 to clear any blockage formed therein and establish a guide for control tube 1703. When the guide wire is fully inserted, the control tube is inserted over the guide wire and then into passageway 210 of the structure. The control tube also has a longitudinal passageway 1706 for receiving the wire guide therein. Also included is wire coil 1704 that is positioned and attached at the distal ends thereof using, for example, silver solder 1705. As previously described with respect to stylet wire 200, control tube 1703 is rotated in a direction opposite that of coiled structure 211 for engaging and expanding wire coil 1704, thereby securing the control tube to the coiled structure.

As depicted in FIG. 18, removal apparatus 1801 includes wire guide 1802 that is inserted into the passageway of the elongated structure. Control tube 1803 includes two longitudinal passageways 1804 and 1805. Passageway 1804 receives the wire guide as the control tube is inserted into the passageway of the elongated structure. Positioned at the distal end of the control tube is inflatable balloon 1806 with passageway 1805 leading thereto through sideport or aperture 1807. To secure the control tube to the elongated structure, a fluid is passed through passageway 1805 to inflate the balloon to an expanded position.

Figure 19:
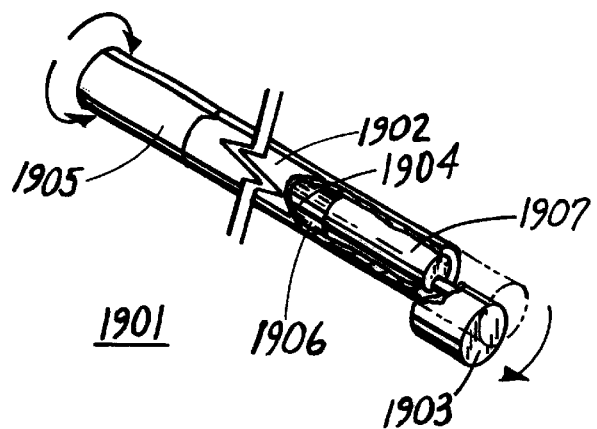
Figure 20:
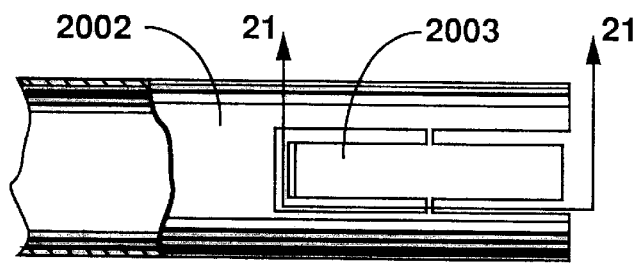
Figure 21:
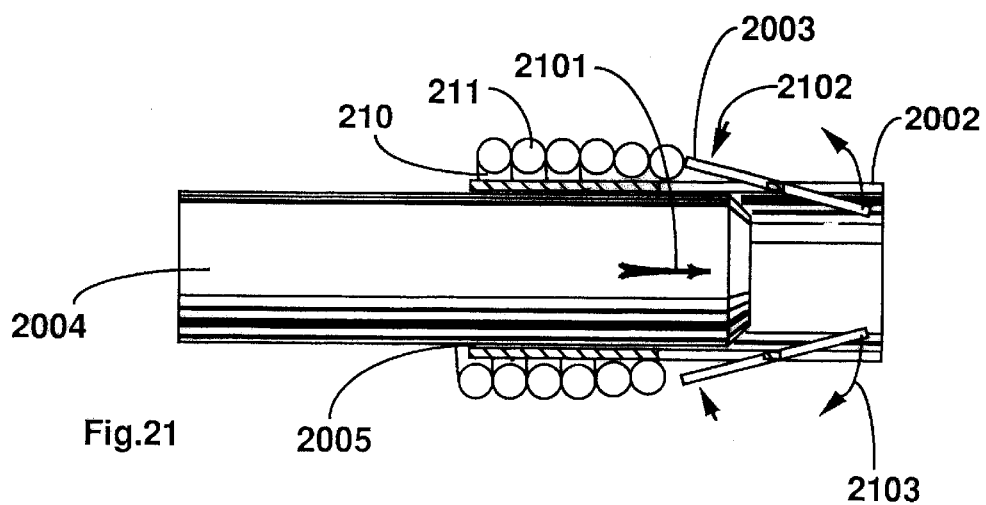

Several other alternative embodiments of illustrative removal apparatus are depicted in FIGS. 19–21. Depicted in FIG. 19 is removal apparatus 1901 that includes control tube 1902 and cylinder 1903. The tube includes longitudinal passageway 1904. Cylinder 1903 is positioned about the distal end of the control tube and rotated to a position off-center of the tube for securing the control tube to the elongated structure. The removal apparatus includes an actuator rod 1904 extending through the control tube and attached to the rotatable cylinder. The rod rotates the cylinder to an off-centered position for securing the control tube to the elongated structure such as the coiled structure of a pacemaker lead Actuator rod 1904 extends between the rotatable cylinder and control mechanism 1905 that is positioned at the proximal end of the control tube. Control mechanism 1905 is rotatable between two positions for rotating the actuator rod and the cylinder between expanded and retracted positions. The actuator rod is attached to the cylinder at an off-centered position to permit rotation of the cylinder and engagement of the elongated structure. Plug 1907 is inserted at the distal end of the tube to maintain the off-centered position of the rod in the passageway.

Depicted in FIG. 20 is illustrative removal apparatus 2001 including a control tube 2002 that has a longitudinal projection 2003 extending at the distal end thereof for securing the control tube to the coiled structure of a pacemaker lead. This arrangement is sometimes referred to as a flea-clip arrangement. Depicted in FIG. 21 is a sectioned view, taken along the lines 21—21 in FIG. 20, of the apparatus in passageway 210 of coiled structure 211. As shown, a stylet wire or rod 2004 is inserted into passageway 2005 of control tube 2002 to engage and retract the extended projections into the wall of the control tube. When the apparatus is inserted to the distal end of the coiled structure, the stylet wire or rod is removed from the passageway of the control tube. As a result, the spring-like projections extend into the coiled structure of the lead, thereby securing the control tube to the coiled structure for controlling the movement thereof. To remove the control tube, the rod is inserted into the control tube passageway as shown by arrow 2101 to again engage the projections. When the rod engages the projections extending into the passageway, the inward extending projections move into the wall in a direction as shown by arrows 2103, whereas the outward extending projections move into the wall in a direction as shown by arrows 2102.

The reader's attention is again referred to the preferred embodiment depicted in FIG. 3. After the stylet wire is secured to the lead and prior to inserting separator tube 212 over the stylet wire and lead, a tie 241 of, for example, nylon cord or suture material is wrapped around proximal end 221 of the lead to secure insulating material 201 to coiled structure 211. The tie controls or limits the movement of the coiled structure within the insulating material. With the insulating material secured to the coiled structure at the proximal end, removal force is applied not only to the coiled structure, but also to the insulating material of the lead as well. This maintains the integrity of the heart lead during subsequent tissue separation from the insulating material. In those instances where the stylet wire has not been fully inserted to the distal end of the lead, the tie also prevents the coiled structure from unraveling, breaking or separating from electrode 220 or the rest of the lead.

As previously suggested, the looped proximal end of the stylet wire can be compressed to permit separator tube 212 to be inserted thereover and over the insulating material of the heart lead. Separator tube 212 comprises a semi-rigid material, such as teflon, for sliding easily through the blood vessel and over the insulating material of the heart lead. In order to place the separator tube over the stylet, the stylet should extend at least 12 inches beyond the person's body so that the looped end can be grasped to apply tension to the stylet. With the teflon separator tube 10 to 12 inches long, the stylet is typically three feet long.

Depicted in FIG. 3 is fibrotic tissue 218 encapsulating heart lead 204. When this occurs in small diameter veins where blood flow has been restricted or prevented, separation and removal of the lead from the tissue is difficult and often causes severe damage or destruction to the vein. Without tension on stylet wire 200, separation is usually not possible in these situations.

Figures 7, 8:
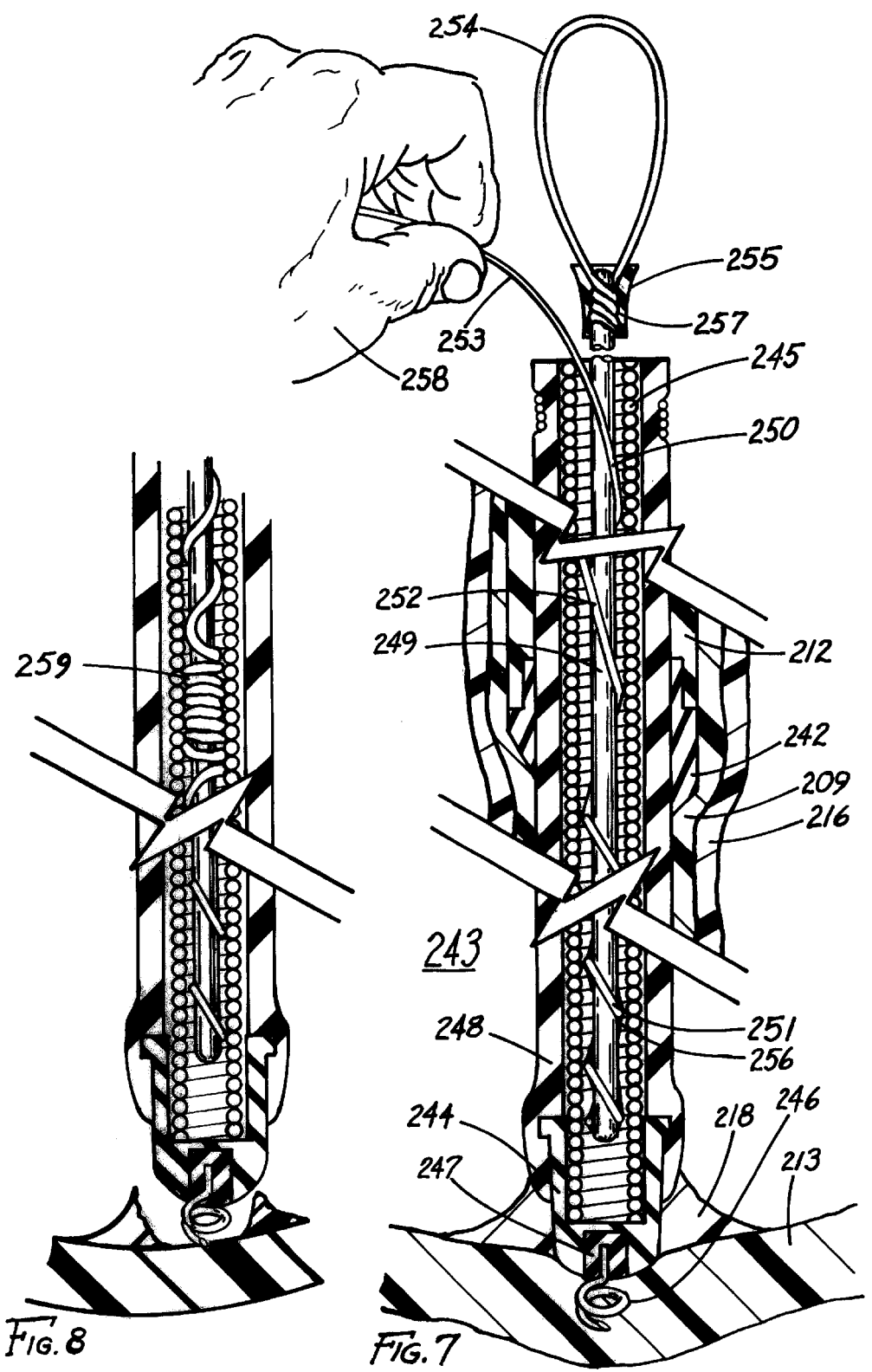
FIG. 7 depicts another embodiment of the lead removal apparatus of this invention.
FIG. 8 depicts the lead removal apparatus of FIG. 7 with the stylet wire secured to the pacemaker lead.

As shown, the distal end of the Teflon separator tube 212 is beveled and includes a cutting edge or edge having a number of teeth for separating heart lead insulating material 201 from encapsulating fibrotic tissue 209. As depicted in FIG. 7, hollow separator tube 212 has a metal beveled tip 242 attached to the distal end thereof with, for example, by a medical grade adhesive. The metal tip provides a more durable edge for separating or cutting encapsulating fibrotic tissue from the lead.

Returning the reader's attention again to FIG. 3, separator tube 212 is moved and rotated along the outer surface of insulating material 201 of the heart lead to separate the lead from the blood vessel wall. After the separator tube has been moved along the entire length of the heart lead, it will abut next to the heart cavity wall as shown by phantom lines 219. The distal end of the heart lead is typically secured to the heart cavity wall by trabeculae or fibrotic tissue 218 that has encapsulated tines 207 positioned at the distal end of the lead. The separator tube 212 is positioned next to the heart cavity wall or pushed slightly while the stylet wire is tensioned in the opposite direction. The separator tube is then rotated back and forth to dislodge and separate tines 207 and the distal end of the heart lead from fibrotic tissue 218 and heart cavity wall 213. As a result, the heart lead has now been completely separated from the blood vessel and the heart cavity wall for subsequent removal. The separator tube, the stylet wire, and the heart lead are then removed from the heart cavity and surrounding blood vessel.

However, should the removal of the heart lead be prevented for whatever reason, the stylet wire is rotated in a clockwise direction to unsecure the stylet and wire coil from the heart lead coiled structure. The time for this operation is lessened by attaching a rotating mechanism such as an electrical screwdriver to the proximal end of the stylet wire.

Figure 27:
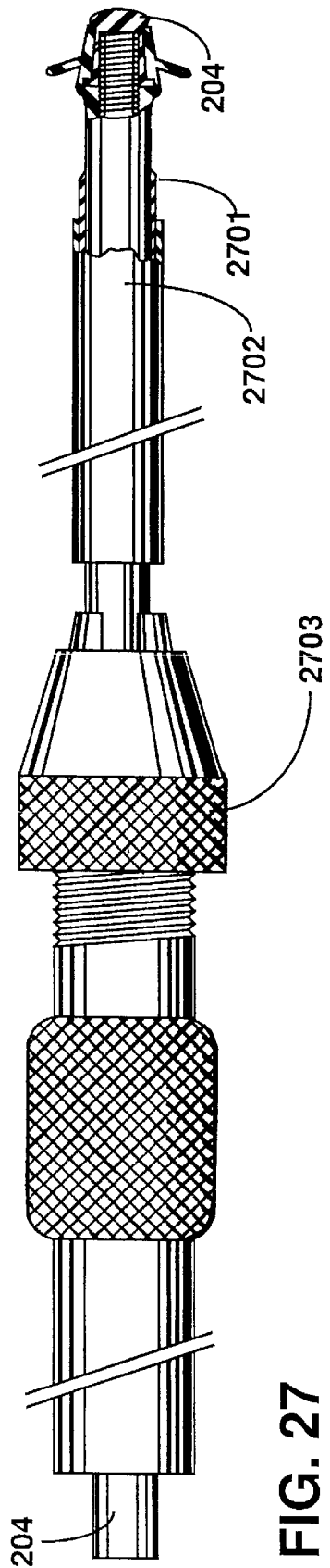

Depicted in FIG. 27 is an alternative embodiment of illustrative separator apparatus 2700. This separator apparatus includes a set of separator and dilator tubes 2701 and 2702 for insertion over pacemaker lead 204. Similar to separator tube 212, separator tube 2701 has a hollow passageway therein for receiving the pacemaker lead. The separator tube is advanced along the lead to engage and separate encapsulating tissue from the lead. Dilator tube 2702 similarly has a hollow passageway therein for receiving separator tube 2701 and the pacemaker lead therein. A preferred material for separator and dilator tubes 2701 and 2702 is polypropylene which is more kink-resistant than Teflon. A polypropylene tube fits easily into the blood vessel for extension to the distal end of the pacemaker lead. Furthermore, the inclusion of approximately 25% of bismuth provides radio-opacity for viewing with, for example, a fluoroscope during insertion of the separator tube. When the dilator tube is inserted over the separator tube and lead, a control mechanism 2703 having a hollow passageway therein is inserted over the lead and connected to the proximal end of separator tube 2101. Control mechanism is well-known as a pinvise and is used for controlling the movement of the separator tube in both a longitudinal and rotational direction. The dilator tube and separator tube are alternatively moved along the lead to first separate the tissue from the lead and further dilate the tissue with the dilator tube. The control mechanism 2103 provides added strength and control during the movement of the separator tube. Dilator tube 2102 not only provides extra dilation of the tissue but also provides additional strength to the entire structure for separating tissue from the pacemaker lead.

Figure 22:
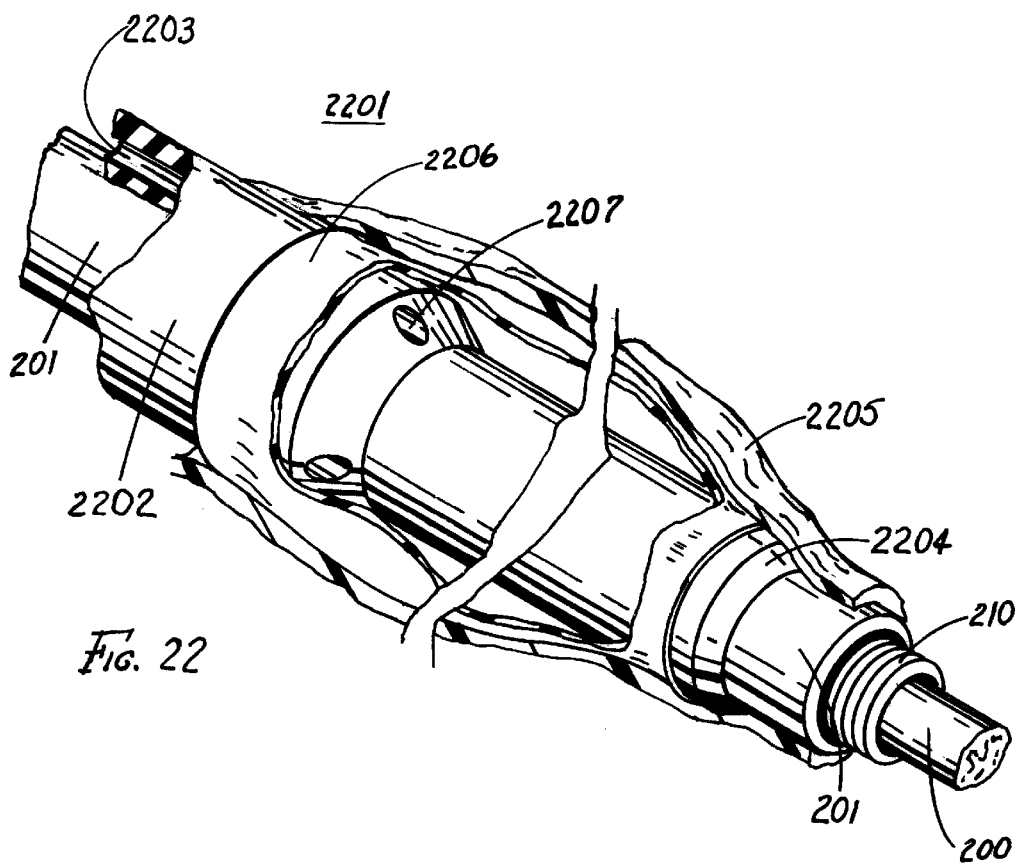
FIGS. 22 and 27 depict alternative embodiments of the apparatus for separating encapsulating tissue from a pacemaker lead of FIG. 3.

Depicted in FIG. 22 is another alternative embodiment of illustrative separator apparatus 2201 for separating encapsulating tissue 2205 from pacemaker lead 204. The separator apparatus 2201 includes a tube 2202 having a longitudinal passageway 2203 therein for receiving and passing over the pacemaker lead including outer insulating material 201. Distal end 2204 of the tube is beveled to provide a wedge for separating encapsulating tissue 2205 from the pacemaker lead. Also positioned and attached in a well-known manner about the distal end of the separator tube is balloon 2206. The tube also includes a plurality of hollow passageways 2207 for supplying a compressed gas or fluid for inflating the balloon. Separator apparatus is inserted over the insulating material sheath of the pacemaker lead to engage encapsulating tissue 2205. The beveled distal end provides a wedge for causing an initial separation of the tissue from the lead. Upon initial contact and separation, the balloon is inflated to provide further dilation and separation of the encapsulating tissue from the pacemaker lead. The balloon is then deflated to permit the beveled distal end to be further moved along the pacemaker lead and engage additional encapsulating tissue. This process is continued until all of the encapsulating tissue is separated from the pacemaker lead.

Depicted in FIG. 24 and is separator apparatus 2401 for separating the distal end of an elongated structure such as electrode tip 220 of pacemaker lead 204 from tissue 218 affixed thereto. This apparatus is particularly advantageous in those instances where the electrode of the pacemaker lead is porous allowing fibrotic tissue to grow therein and secure the electrode tip thereto. Separator apparatus includes a first tube 2402 having a hollow passageway 2403 for receiving pacemaker lead 204 and extending to the distal end thereof. Attached to the distal end of the first tube 2402 is an elongated member such as stainless steel wire 2404. The first tube wall also has a hollow channel or passageway 2408 extending longitudinally therethrough for passing the wire the entire length of the tube. Alternatively, the stainless steel wire can be affixed to the distal end using any suitable well-known fastening means. A second tube 2405 also has a longitudinal passageway 2406 for receiving the first tube. In addition, the second tube similarly includes a hollow channel or passageway 2407 for extending stainless steel wire 2404 through the entire length of the tube and beyond the proximal end thereof. This permits the loose end of the wire to be controlled by the clinician to remove the distal end of the pacemaker lead from the encapsulating or affixed tissue. As shown in FIG. 25, the first tube is extended to the distal end of the pacemaker lead and placed next to electrode 220. The second tube with the stainless steel wire is then also positioned next to the distal end of the pacemaker lead next to the electrode. The clinician puts tension on the stainless steel cutting wire and then rotates the second tube relative to the first causing the stainless steel wire to wipe across the face of the electrode as shown. Rotation of the two tubes are shown by arrows 2501 and 2502. This wiping motion across the pacemaker electrode literally cuts the electrode tip free from the encapsulating or affixed tissue 218. Instead of stainless steel wire, suture material is also used to perform the cutting action.

Depicted in FIG. 26 is a second alternative embodiment of illustrative separator apparatus 2601 for separating the distal end of a pacemaker lead having a plurality of tines such as tines 207 of pacemaker lead 204 encapsulated in fibrotic heart tissue 218. Apparatus 2601 includes tube 2602 having a longitudinal passageway 2605 for receiving pacemaker lead 204. The tube is inserted over the lead and extended to the distal end thereof. The tube includes a plurality of slots 2603 formed at the distal end for receiving pacemaker lead tines 207. When the tines are received in the slots, tube 2602 is rotated back and forth in a circular motion for dislodging and separating the tines from the encapsulating tissue 218 extending from heart wall tissue 213.

Depicted in FIG. 7 is another illustrative embodiment of the lead removal apparatus of this invention. In this embodiment, pacemaker lead 243 is similar to the lead shown in FIG. 3; however, the distal end of the lead is of a different configuration. In particular, electrode 244 has two cavities therein. One cavity is for receiving the coiled structure 245 of the lead. The second cavity is for receiving and securing anchoring coil 246 secured in the cavity with insulating material 247 in a well-known manner. The distal end of anchoring coil 246 is cut to form a beveled or sharpened edge for turning or corkscrewing the coil into heart cavity wall 213. Anchoring coil 246, as a result, securely attaches electrode 244 to the heart tissue to establish good electrical contact for stimulating the heart tissue with electrical pacing pulses from the pacemaker Insulating material 248 surrounds coiled structure 245 and partially surrounds electrode 244. Since anchoring coil 246 is utilized in this configuration, the insulating material is molded over the coiled structure and electrode without forming tines for the endothelial tissue to form therearound.

Stylet wire 249 of this lead removal apparatus and lock wire 250 attached to the distal end thereof have a combined diameter much less than the inside diameter of coil structure 245 of the lead. This is particularly advantageous for those situations when the coiled structure of the lead has been deformed, unraveled, or in some way damaged. In this embodiment, lock wire 250 has a plurality of turns 251 wrapped around the distal end of the stylet wire. Turns 251 of the lock wire at the distal end of the stylet wire are closely wrapped and attached to the distal end of the stylet wire using, for example, a silver solder. Turns 252 of the lock wire are more loosely wrapped and are approximately 75 in number. The unwrapped proximal end 253 of the lock wire extends beyond the passageway of the lead and is secured and positioned by, for example, the physician's hand 258 when the stylet wire is rotated to expand lock wire turns 252 and engage the turns of coiled structure 245.

Control mechanism 254 such as a loop of malleable wire is wrapped around and secured to the proximal end of the stylet wire using, for example, silver solder 257. Slidable chuck 240 is also suitable for use as the control mechanism for stylet wire 249. A Teflon coating 255 surrounds the interconnection to prevent possible injury to the physician or patient. Control loop 254 is provided for the physician to move the stylet wire in and out of the passageway of the lead as well as rotate the stylet wire to engage the coiled structure of the lead. When the stylet wire is secured to the pacemaker lead, loop 254 is used to extract stylet wire and pacemaker lead from the patient.

To unravel the turns of the lock wire, a tool such as an electrical screwdriver is attached to the control mechanism loop to rotate the stylet wire and expand the turns of the lock wire. While the stylet wire is being rotated, the physician secures the position of the proximal end 253 of the lock wire to permit lock wire turns 252 to tangle and form a bundle 259 that engages the coiled structure as depicted in FIG. 8. The stylet may have to rotate 50 to 100 turns to form bundle 259 and engage coiled structure 245.

After the lock wire has secured the stylet wire to the pacemaker lead, the physician grasps control loop 254 and continues to rotate the stylet wire and pacemaker lead to dislodge anchoring coil 246 from the heart tissue. Should the blood vessels encapsulate the pacemaker lead, separator tube 212 is inserted over the stylet wire and pacemaker lead as previously described to separate the lead from the encapsulating blood vessel tissue.

The separator tube may also be extended to the distal end of the pacemaker lead to turn and dislodge the distal end of the pacemaker lead from the heart tissue.

FIGS. 32 and 33 depict another embodiment of the lead removal apparatus 3201 of the present invention. Although designated as a lead removal apparatus, this apparatus can similarly be designated as an extraction device 3201 for removing an implanted lead such as a cardiac lead which has been implanted in biological tissue or, more particularly, cardiac tissue. The lead includes a coiled structure 211 having a passageway 210 extending longitudinally therein. The lead removal apparatus comprises a tube 3202 having a longitudinal passageway 3218 extending longitudinally therein through which a control means 3203 and, in particular, a stylet 3210 extends and is moveable therein. As suggested, the control means is slidably arranged in the control tube 3202 and has a distal end 3204 that is configured for insertion into the passageway of the coiled structure. The lead removal apparatus also comprises expandable means 3205 other than and separate from the control tube and is positioned proximate distal end 3204 of the control means. The expandable means has an expanded position in the passageway of the coiled structure for securing the control means to the coiled structure and subsequent removal from the biological tissue. The expandable means, or outwardly expandable unit 3205, includes a laterally flexible member 3206 that extends longitudinally and proximally from the distal end of the control means. This laterally flexible member has a proximal end 3207 for assuming an expanded position of the expandable means and engaging the coiled structure. The distal end 3208 of the laterally flexible member is attached to the control means or style using, for example, silver solder.

The lead removal apparatus 3201 further includes a sleeve 3209 positioned around the laterally flexible member and the control means and, in particular, stylet 3210. In the particular embodiment depicted in FIGS. 32 and 33, the distal portion of stylet 3210 is ground to a semicircular shape so as to facilitate insertion in sleeve 3209. The laterally flexible member 3206 is formed from the stylet 3210 by folding the stylet back on itself about distal end 3204 thereof, forming folded back portion 3211 of the stylet. The sleeve 3209 and the semicircular shape of the stylet accommodates electrical leads having minimally sized passageways 210.

Figure 36:
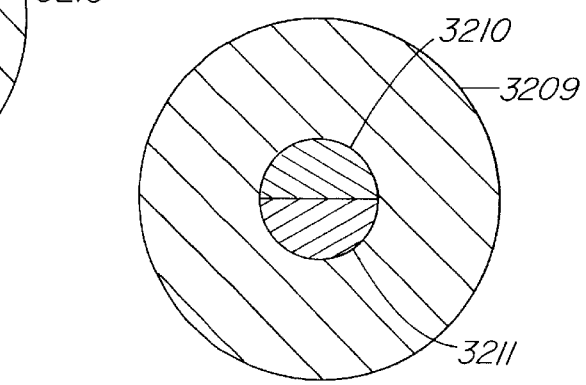
FIG. 36 depicts an enlarged, cross-sectional view of the expandable unit of the lead removal apparatus of FIG. 32 taken along the line 36—36.

FIG. 36 depicts an enlarged cross-sectional view of the lead removal apparatus of FIGS. 32 and 33 taken along the line 36—36. Sleeve 3209 comprises a stainless steel cannula of which stylet 3210 and folded back portion 3211 are positioned in the passageway thereof. The sleeve is secured to the folded-back portion and the stylet using, for example, silver solder as previously suggested.

Figure 35:
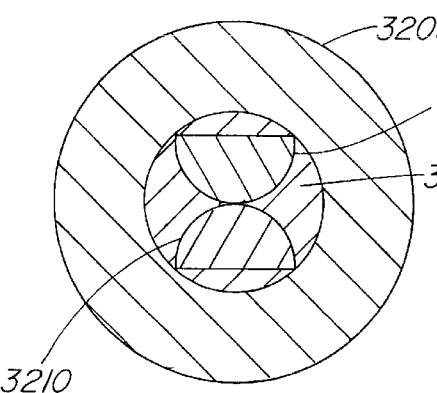
FIG. 35 depicts an alternative embodiment of an enlarged, cross-sectional view of the sleeve and stylet of FIG. 32.

FIG. 35 depicts an alternative embodiment of stylet 3210 and folded-back portion 3211 in sleeve 3209. In this particular configuration, the semicircular curved portions of the stylet and folded-back portion are placed in contact with each other and inserted in the passageway of the sleeve. This particular configuration would accommodate an electrical lead having a larger passageway 210 extending therein. Again, stylet 3210 and folded back portion 3211 are securely positioned in the passageway of the sleeve using, for example, silver solder 3219.

FIG. 33 depicts lead removal apparatus 3201 of FIG. 32 in which expandable means 3205 is in an expanded position. The lead removal apparatus includes handle 3214 positioned at the proximal end 3215 of the stylet 3210 and a handle 3216 positioned at proximal end 3217 of control tube 3202. As depicted in FIG. 32, the relative longitudinal position of handles 3214 and 3216 are locked in place using lock 3213 such as a pin positioned transversely therethrough. When operating lead removal apparatus 3201, lock 3213 is removed from the two handles, and handle 3216 is urged forward in a distal direction with respect to handle 3214 of the stylet. This causes control tube 3202 to engage laterally flexible member 3206 and urge laterally flexible member 3206 to an expanded position to engage the turns of coiled structure 211.

Figure 34:
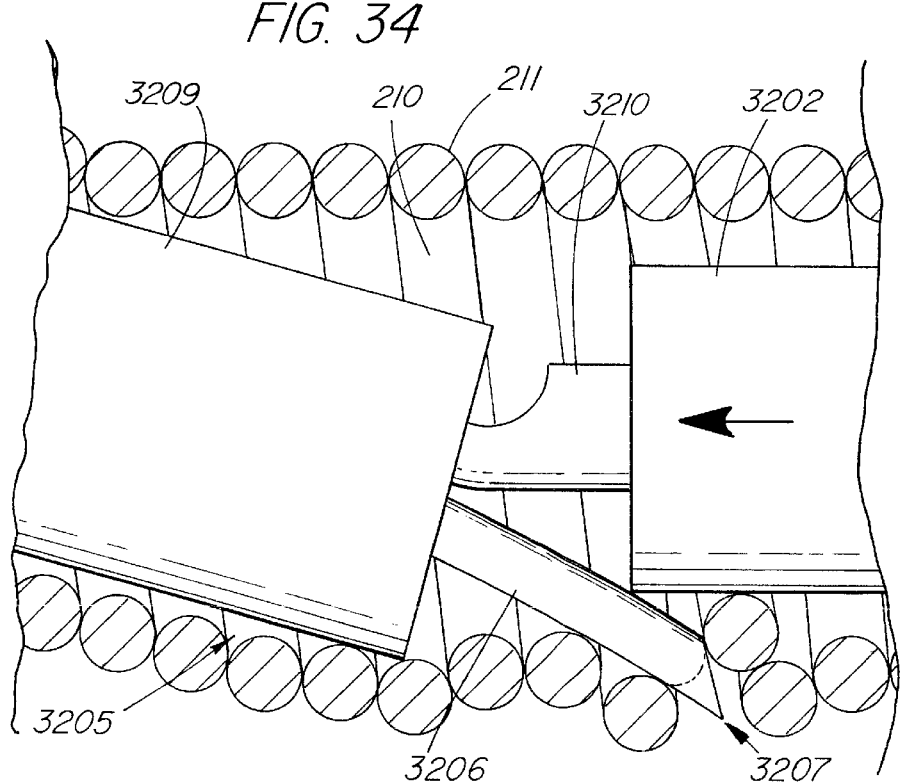
FIG. 34 depicts an enlarged, partially sectioned view of a portion of the expandable means or unit of the lead removal apparatus of FIG. 33.

FIG. 34 depicts an enlarged view of expandable means 3205 of the lead removal apparatus of FIG. 33. This enlarged view more clearly indicates that the longitudinal movement of control tube 3202 causes the lateral flexure of laterally flexible member 3206 to engage the turns of coiled structure 211. As indicated, proximal end 3207 of the laterally flexible member is beveled so as to facilitate easy engagement of coiled structure 211. Furthermore, one or more turns of the coiled structure are engaged between the proximal end 3207 of the laterally flexible member and control tube 3202. This engagement provides secure engagement of the laterally flexible member with the coiled structure without unduly deforming the coiled structure into passageway 210 of the coiled structure. As indicated, the engaged turns of the coiled structure are fixed between control tube 3202 and laterally flexible member 3206.

FIG. 39 depicts an enlarged, partially sectioned side view of control tube 3202 and stylet 3210 of FIG. 33. Stylet 3210 includes two right angle bends 3220 and 3221 for engaging the internal walls of the control tube. When control tube 3202 is advanced distally with respect to stylet 3210, these right angle bends help maintain the relative position of the control tube and stylet when the control tube is engaging laterally flexible member 3206.

FIG. 37 depicts an alternative embodiment of control means 3205 of lead removal apparatus 3301 of FIG. 32. Expandable means 3205 or outwardly expandable unit 3205 includes the distal portion of stylet 3210 having a plurality of folded-back portions 3212. The proximal end of the plurality of folded-back portions 3212 forms laterally flexible member 3206. As previously suggested, sleeve 3209 is positioned around stylet 3210 and the plurality of folded-back portions to maintain the laterally flexible member in a fixed relative position.

FIG. 38 depicts an enlarged, cross-sectional view of expandable means 3205 of FIG. 37 taken along the line 38—38. This enlarged view shows that plurality 3212 includes two folded-back portions contained in the passageway of sleeve 3209 and held in place using silver solder 3219. The use of a plurality of folded-back portions allows the use of a larger sleeve and a larger diameter stylet for engaging coiled structures having a larger passageway 210 than previously described for the embodiment of FIG. 32.

FIGS. 40–44 depict alternative embodiments of a lead removal apparatus, such as a locking stylet 510, that comprises a stylet 511, an actuator portion 512, such as an elongate cannula that is slidably disposed thereover, and an expandable portion 513 attached about the distal portion 560 of the stylet 511. With the locking stylet 510 having been advanced into the coil of a pacemaker lead (see discussion of FIG. 44) such that the expandable portion 513, preferably comprising a plurality of expandable members 514, is situated near the distal tip of the pacemaker lead, the actuator portion 512 (also referred to in other embodiments as the control mechanism) is manually advanced over the stylet 511 until the distal end 539 of the actuator portion 512 contacts the proximal end 545 of the expandable portion 513. The plurality of expandable members 514 plastically or elastically deform as the expandable portion 513 is longitudinally compressed, at least some of them eventually bowing outward until contacting and engaging the coils of the pacemaker lead. The expandable members 514 provide a positive fixation against and/or between the coils which allows the stylet 511 retract the pacemaker lead from the cardiac or scar tissue into which it has been at least partially ensnared. This positive fixation or biting engagement in the proximal direction allows the lead to be pulled proximally to allow surrounding tissue to be dilated or removed from the encapsulated lead. Testing has shown that a locking stylet 510 such as that depicted in FIG. 40 has a pull strength of up to approximately 15 pounds, more than sufficient to provide the traction needed to free the lead, absent complicating factors such as extensive formation of scar tissue along the length of the lead.

FIG. 40 depicts an embodiment of the locking stylet 510 in which the expandable portion 513 comprises a multifilar wire bundle 515 that comprises a series of adjacent windings 570 helically wrapped around the style 511 and affixed thereto. In the illustrative embodiment, the multifilar wire bundle 515 includes six individual expandable members 514 that comprise helically wound metal wires; however any practical number of wires can be used. It has been found that using a multifilar wire bundle 515, rather than a single helically wound wire, allows for greater expansion. This results in having a 0.015" OD locking stylet that can expand to a sufficient diameter to engage and remove the complete array of standard pacemaker leads where the range of coil lumen diameters is typically 0.016" to 0.032" (approximately 0.4 to 0.9 mm). The term 'engage' as used within the portion of the specification describing the embodiments shown in FIGS. 40–47, is defined as a situation in which the expandable members 514 displace, shift, or otherwise intersperse with selected ones of the pacemaker lead coils 548 in manner that forms a locking interaction or biting engagment. This contrasts with certain prior art devices in which the interaction between the lead removal apparatus and the pacemaker coils is primarily a frictional relationship. As shown in FIG. 41, one method of forming the multifilar wire bundle 515 is to helically wind the six individual wires 514 together over a pin 541 in the configuration that will ultimately be attached distally to the stylet 511. The individual wires 514 can be soldered together, if so desired, at their proximal end, which in that case, the pin 541 should be made of titanium or nitinol such that the solder will not stick. Once helically wound, the multifilar wire bundle 515 is inserted over the stylet 511 as shown in FIG. 40. The expandable portion 513 comprising the multifilar wire bundle 515 of the illustrative embodiment is divided into three main sections. The distal section 517 includes a relatively tight wound wrapping of a multifilar wire bundle 515 that is affixed to the stylet 511 about the distal end 516 of the locking stylet 510 with a distal fixation joint 5such as a solder joint, a crimped band, or some other well-known attachment of fixation means. In the intermediate section 518, the multifilar wire bundle 515 of the illustrative embodiment is wound more loosely (i.e., with a greater pitch) to permit greater expansion during deployment. While the individual wires 514 of the multifilar wire bundle 515 are kept tightly together within the bundle, the gaps 553 between the windings 570 of adjacent multifilar wire bundles 515 increase over that of the distal section 517, in which the gaps 553 are generally minimal (e.g., 0.0035") to nonexistent. The pitch 557 of an individually wound wire 514 can vary within the immediate section 518, depending on a number of parameters (number of wires, wire diameter, etc.) and the range of expansion desired. In the illustrative embodiment with an approximately 3" (7.6 cm) expandable portion that includes a six-wire bundle 515 of 0.004" stainless steel wire, the multifilar wire bundles 515, which measures approximately 0.024" in width, include an increasing pitch 557 toward the center 554 of the intermediate section 518, with a maximum pitch 557 of approximately 0.12". The gaps 553 between the mutlifilar wire bundles 516 become progressively narrower in width toward the proximal half of the intermediate section 518. In the proximal section 519 of the illustrative embodiment, the windings 570 of the mutifilar wire bundle 514 include gaps 553 essentially disappear such that the individual bundles 515 are not readily discernable. These dimensions are merely exemplary and can be varied according to the various structural parameters selected and the desired performance characteristics of the lead extraction apparatus 510. At the proximal end 545 of the expandable portion 513, a proximal fixation joint 521, such as a silver solder joint or other bonding means, may be included, however, it is not essential or necessary for the expandable portion 513 to properly function. Unlike the distal fixation joint 521, only the individual wires 514 are soldered together in a proximal fixation joint 521, leaving the expandable portion 513 free to slide over the stylet 511 at that point. An optional ring, section of cannula, or other structure can be attached to the proximal end 545 of the expandable portion 513 to provide a surface against which the actuator portion 512 may contact.

In the illustrative embodiment, the stylet 511 comprises a 0.0075" 304 stainless steel spring tempered wire with a tensile strength of 382/455 ksi. The actuator portion 512 comprises a thin wall cannula, such as a 28 gauge hypodermic needle cannula. The length of the actuator portion 512 is approximately 60 cm from the distal end 539 to the distal handle 522 to which it is affixed. The wire 514 used is 0.0035–0.004" annealed 304 stainless steel wire. The combination of a 0.0075" stylet 511 and 0.004" wire 514 yields a device having a 0.0155" OD, which is about the practical upper limit if the device is to be used within a 0.016" ID pacemaker coil. If the 0.004" wire exceeds tolerances, e.g., more than 0.0002", the device may not fit within the smaller size pacemaker lead and one would not have a device that would readily fit within the normal range of pacemaker leads sizes.

Figure 47:
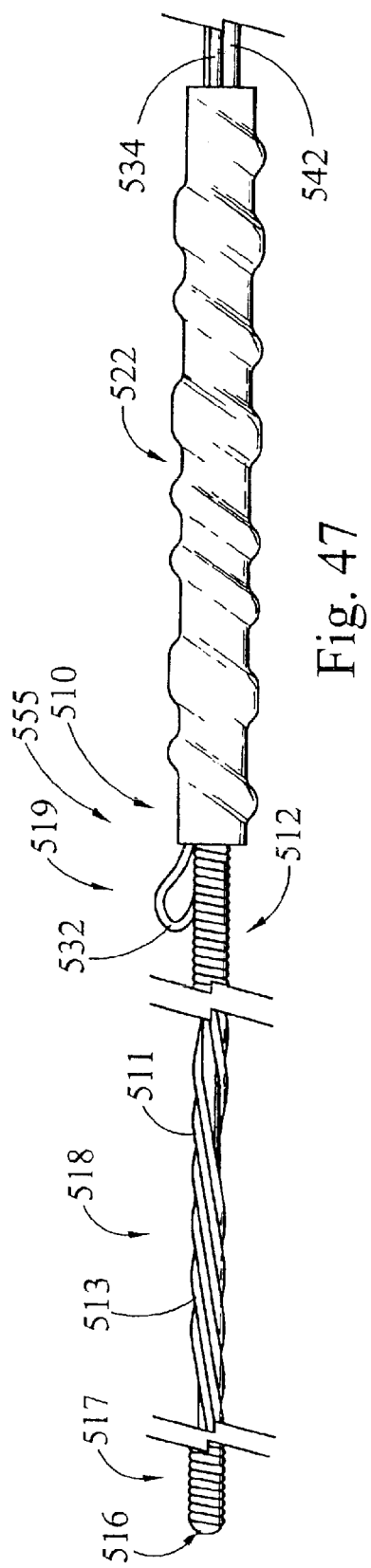
FIG. 47 depicts a side view of a side view of an embodiment of the present invention in which the expandable portion and actuator portion form an unitary structure.

The expandable portion 513, being approximately 3 inches long, comprises a distal section 517, intermediate section 518, and proximal section 518 measuring approximately 0.6", 2.2", and 0.3", respectively. The dimensions of the expandable portion 513 can be quite variable; however, a 3" length ensures adequate expansion to remove both smaller and larger sized pacemaker leads. The overall length of the locking stylet in FIG. 40 is approximately 140 cm. As depicted in FIG. 47, the proximal section 519 of the expandable portion 513 can be greatly lengthened and modified to also function as an integral actuator portion 512 to compress and expand the intermediate section 518. In this modification, the actuator portion 512, now a coil of helical wires rather than a solid cannula, would be integral with the expandable portion 513. Of course, the actuator portion 512 could comprise a coil and still be separate from the expandable member 513 (similar to the embodiment of FIG. 40). Another alternative is for the actuator portion to be a braided tube of metal, plastic, or some other material. In each of these embodiments, handles 522, 523, which are used to facilitate advancement of the actuator portion 512, and other features shown in FIG. 40 could essentially remain the same as the illustrative embodiment, if desired.

As previously noted, the configuration of the expandable portion 513 is variable, largely depending on materials of its construction. It is preferred that the wire 514 be annealed; however, it is possible that only a selected portion of the expandable portion 513, e.g., the intermediate section 518, be annealed, or it is possible to have different degrees of annealing across the length of the expandable portion. While the illustrative embodiment utilizes round wire, wires with alternate cross-sectional geometries (e.g., square, triangular, flattened, etc.) may be used to provide different properties for expanding and engaging the coils of the lead. Other features could be incorporated such as altering the surface properties of the wire by adding roughness or applying a polymeric coating that could possibly improving engagement with the coils. Yet another embodiment would be to include wires with different physical properties within a single multifilar wire bundle 514.

Again referring to FIG. 40, an optional feature is depicted in which the actuator portion 512 is secured in place to prevent advancement against the expandable portion 513. To accomplish this, the illustrative embodiment includes a deployment guard 534, such as a ligature, that is affixed to both the distal handle 522 affixed to the actuator portion 512, and a proximal handle 523 that is affixed to the stylet 511. The distal half 535 of the ligature is secured to the actuator portion 512 with distal knot 526 or other well-known means of attachment. Optionally, an end of the distal half 535 can extend distally from the distal end 555 of the distal handle 522 to form an exposed attachment loop 532 to which the physician can tie a suture that also is externally secured to the pacemaker lead for providing additional tractile force. A second knot 572 helps prevent the attachment loop 532 from coming apart when the deployment guard 534 is severed. The distal handle 522 of the illustrative embodiment comprises a section of shrink wrap 527 that is heat shrunk over the actuator portion 512 and a section of wrapped wire 540 placed thereover, but underneath the shrink wrap 527, to advantageously improve the ability of the operator to grip the handle 522. Additionally, the shrink wrap 527 further secures the distal knot 536. The distal half 535 and the proximal half 536 of the ligature 534 are either joined by, or bisected by a central knot 537, which in the illustrative embodiment, includes a second piece of ligature 573 that permits the operator to pull the main ligature 534 away from the stylet 511 to be cut. In the illustrative embodiment of FIG. 40, the stylet 511 is further protected by a stylet guard 542 that represents a proximal extension of the actuator portion 512 cannula, which surrounds the otherwise-exposed stylet between the distal and proximal handles 522, 523. This stylet guard 542 can also comprise a separate component from the actuator portion 512, particularly in the embodiment of FIG. 47, in which the actuator portion 512 and expandable portion 513 are combined. The proximal half 536 of the ligature 534 is secured to the stylet 511 using a proximal knot 528. Alternatively, a single piece of ligature can be used, or the ligature can be detachable in a manner that does not require that it be severed (i.e., a knot to be untied or another detachable configuration).

The proximal handle 523 encases the proximal knot 528 and also provides fixation for proximal portion 524 of the handle 523. The illustrative proximal portion 524 comprises a single twisted length of wire 556, typically extending at least 30–40 cm, and preferably about 60–65 cm, beyond the proximal handle 523 that serves as an extension of the stylet 511 and functions much like a handle to allow the operator to create traction on the locking stylet 511, such as when placing a dilator sheath thereover. In fact, it is conceivable that the stylet 511 itself can be extended proximally and actually become the proximal handle 523 and the proximal portion 524. The proximal portion 524 is sized and configured such that it can be manipulated by the operator without requiring the assistance of another individual, while still enabling the operator to maintain the entire apparatus 510 within the sterile field. In the illustrative embodiment of FIG. 40, the proximal portion 524, which includes an end loop 525 at the proximal end 533 of the locking stylet 10, is shown in an uncoiled or straight configuration 567. The first end 529 of the twisted wire 556 is laid overlapping the stylet 511, while the second end 530 of the twisted wire 556 is wound around both, also providing a grip to the proximal handle 523. A fixation joint 531, such as a solder joint, measuring about 0.5" in length, secures the two ends, 529, 530 and stylet 511 together with the shrink wrap 527 of the proximal handle 523 helping to provide further fixation and reinforcement. While the illustrative examples are simple in their construction, it should be noted that distal and proximal handles 522, 523 can assume a wide variety of configurations and be formed from a variety of materials, e.g., molded plastic components attached to the actuator portion 512 and stylet 511, respectively.

The proximal end 538 of the actuator portion 512 extends proximally to the distal end 557 to the distal handle 522 to protect the stylet 511 when the ligature 534 is cut to allow forward advancement of the actuator portion 512. Many possible alternative deployment guards 534 for preventing premature forward advancement of the actuator portion 512 should be obvious to the skilled artisan. For example, the distal and proximal handles 522, 523 can be locked together with a pull pin, adhesive pull strip, or one of a multitude of known fixation means.

FIGS. 42–43 depict embodiments related to that of FIG. 40. In the embodiment of FIG. 42, the expandable portion 513, comprises expandable members 514 that include a plurality 544 of substantially parallel wires that are affixed both distally and proximally with fixation joints 520, 521, such as silver solder. The individual wires 514 bow outward as the expandable portion 513 is compressed by the advancement of the actuator portion 512, thereby providing an radial expansile force, whereby the expandable members 14 engage the coils of the pacemaker lead. As with the embodiment of FIG. 40, the wire 514 is typically annealed, such that it can easily deform to allow the expandable member 513 to compress. Alternatively, the wires 514 can be formed with slight kinks or scores within the surface thereof, to facilitate bending during deployment.

The expandable portion 513 depicted in FIG. 43 includes a cannula that includes a series of longitudinal slots 543 that form a like number of expandable members 514. As with the embodiments of FIGS. 40 and 42, compression of the expandable member 513 results in deformation of the expandable members 514 which in turn, contact and engage with the coils of the pacemaker lead to permit its removal from the patient. In addition to having parallel slots 543 as shown, the slots 543 could be of a helical or spiraled configuration. A second inner cannula could be used in conjunction with the first cannula, the second having a different configuration of slots to compliment or enhance the function of the first cannula. It is also possible to combine wound wire with a cannula to form the expandable portion 513. It possible to conceive of an almost unlimited number of different configurations of the expandable portion 513 that would allow a series of expandable members 544 to be compressed via an actuator portion 512 and plastically or elastically deformed outwardly to engage the coils of an ensnared lead, thereby assisting in its removal from body tissue. Any such embodiment should be considered to fall within the scope of the current invention.

FIG. 44 depicts the locking stylet 511 of FIG. 40 following deployment within a pacemaker lead 546. As the actuator portion 512 is advanced through the coils 548 of the pacemaker lead 546, over the stylet 511, it contacts the proximal edge 545 of the expandable portion 513. Further advancement of the actuator portion 512 forces the expandable portion 513 to become longitudinally compressed. As the expandable portion 513 becomes longitudinally compressed, one or more of the individual wires 514 comprising the expandable portion 513 will 'pop out' or kink and extend outward from the mulitfilar bundle 515 and stylet 511 as longitudinal force is applied. As the gaps 553 between the helical windings 570 narrow and addition wires 514 deform outward, the expandable portion 513 is compressed further. In a larger sized pacemaker lead, for example, the expandable portion 513 may be compressed in length from 3" down to about 0.5". This causes the unsecured expandable members 544 of the intermediate section 518 to unwind as they plastically deform, thereby expanding outward to contact the coils 548 and push them outward against the outer insulation 547 of the pacemaker lead 546. The expansile force of the expandable members 544 often results in the individual wires being pressure into, and some cases, through the spaces 550 between the coil turns, thereby increasing the fixation between locking stylet 510 and the pacemaker lead 546. Generally, mere frictional engagement between the device and coils 548 is not sufficient to allow the lead to be removed from the patient since the force required typically cannot be achieved before the frictional engagement fails. The fact that the coils 548 themselves are typically multifilar, acts to improve the fixation, compared to an lead embodiment having a single coiled electrode wire. As depicted, a section 565 of four multifilar coils 548 is generally shifted outward as group, as the wires 514 of the expandable portion apply sufficient force that particular section 565. The adjacent section 566, which is not being impinged by the expanding wires 514, remains in its original position, thereby creating a 'shoulder' at the junction 569 between the two adjacent sections 565, 566, this shoulder facilitating positive fixation of the lead when traction is applied. The actuator portion 512 is advanced until resistance is met from the expandable portion 513 being unable to further compress. Depending on the size of the coil lumen 551 and the number of wires 512 in the multifilar wire bundle 515, the expandable members 544 can compress and deform both outward and inward to form at least one irregular-shaped expanded mass 549 of deformed wires. If the device 510 is being deployed in a smaller lumen pacemaker lead 546, e.g., 0.016", it requires fewer wires 514 deforming outward to successfully engage the coils 548 and in fact, a large expanded mass 549 which is generally required for engaging larger lumen leads, would not have an opportunity to form given the space limitations. The random and irregular geometry of the protruding wires 514 that eventually comprise the expanded mass 549 with its twisted bends and interlocking wires, improves fixation compared to expandable members 544 with regular curved geometries.

The multifilar wire bundle 515 also acts to increase the mass needed to fill larger coil lumens which may have up to 4 times the cross-sectional area, thereby permitting one size of locking stylet 510 to work for both smaller and larger size coils. The shape of the expandable mass 549 can vary widely, depending on how it is formed and deployed. For example, in smaller diameter coil lumens 551, the expandable portion 513 may form more than one smaller expanded mass 549, rather than one large one. It should be noted that hand winding of the mutifilar wire bundles 515 adds to irregularity of the expanded mass 549 shape over that which would result from the bundles being machine wound.

FIG. 46 depicts an embodiment in which the proximal handle 523 includes an elongated proximal portion 524 in a pre-shaped or preformed first configuration 561 which represents the relaxed state of the proximal portion 524. In the illustrative embodiment, the first configuration 561 is preformed such that the intertwined wire 556 comprises a compacted arrangement, such as the illustrative plurality of coiled loops 562 (e.g., 3–4). The illustrative first configuration 561 conveniently provides the operator an improved configuration for gripping the apparatus 510, such as through the aperture 571 formed by the loops 562, and more importantly, to be able to maintain the proximal portion 524 in a more compact and manageable configuration to reduce the likelihood of a portion thereof passing beyond the outer edge 564 of sterile field 563. Without the compact, preshaped configuration 561, a second person is typically required to hold and maintain the proximal portion 524 within the sterile field 563. As noted, the proximal portion 524 is made particularly long, in part, to permit the operator to manipulate or uncoil the proximal portion 524 into a second configuration 567 (depicted in FIG. 40) which is sufficiently straight to allow a medical device (not shown) having a passageway, such as a dilator sheath, to be fed thereover, usually for purposes of assisting in the loosening of scar tissue along the lead path. The proximal portion 524 can either be constrained by operator into the second configuration 567, or it can be done so by feeding the sheath or other medical device over the proximal portion 524. The first configuration 561, as used herein, represents a compacted configuration that includes an overall diameter in its widest plane, including any coils, turns, and bends, that exceeds the passageway diameter of a standard medical device, such as a dilator sheath. The second configuration 567, as used herein, includes a sufficiently straight configuration (not necessarily being substantially straight) such that a standard medical device, such as a dilator sheath, can be advanced over the proximal portion without a large degree of difficulty.

In the embodiment of FIG. 40, the second configuration 567 may represent the relaxed state, in contrast to the embodiment of FIG. 46, which requires manipulation by the operator, to attain a substantially straightened configuration. Preferably, but not essentially, the proximal portion 524 is designed such that once the medical device has passed thereover, the proximal portion 524 tends to resiliently return substantially to the first, compacted configuration 561, although it is typical that a certain amount of plastic deformation occurs such that the original shape is not attained. By adding shape memory to the proximal portion 524 by winding the intertwined wire 556 around a fixture to form a series of coiled loops 562, the operator can conveniently unwind the proximal portion 524 in a controlled manner and without assistance as the sheath is fed and advanced over the proximal end 533 of the apparatus 510. It is particularly advantageous to have the proximal end 533 of the apparatus in relative proximity to the point at which the operator grasps the apparatus 510, as opposed to having to feed the sheath over the proximal end 533 of an uncoiled proximal portion 524 that can be 50–60 cm or more away, something that at best, is difficult to do without allowing a portion of the proximal portion 524 to inadvertently leave the sterile field 563 or contact a non-sterile surface. While the pre-shaped configuration 561 of the illustrative embodiment, comprising coiled loops 562, represents one preferred embodiment, it should be noted that other preformed shapes (e.g., a serpentine configuration) can be fashioned in order to achieve the desired goal, reducing the proximal portion 524 to a manageable configuration that can be manipulated by a single operation. Additional components may also be included, such as clips, housings, etc.) which cooperate with the proximal portion 524 to achieve a compact state, and that still permit passage of a sheath thereover. Not only does the pre-shaped or coiled proximal portion 524 of the handle 523 have utility in each of the illustrative embodiments, conceivably, any apparatus constructed for removing elongated structures, such as pacemaker and defibrillator leads, catheters, and the like, can be modified to include a compacted or pre-shaped elongated handle which can function for any of the purposes described above. As used herein, the proximal handle 523 is a common element of all lead extraction devices that are manually manipulated by an operator, with the proximal portion 524 being a component thereof for purposes of nomenclature. The illustrative proximal handle 523 is exemplary, and it should be noted that the proximal handle 523 and proximal portion 524 may represent a common element in some embodiments, especially if the coiled configuration 561 is used as the sole means by which the operator grips and applies traction to the apparatus 510. Additionally, the distal handle 522 of the illustrative embodiments of FIGS. 40–47 is not necessarily present in all embodiments that utilize the coiled configuration of the proximal handle 523 and proximal portion 524, particularly those which lack an actuator portion 512.

Of course, it will be understood that the aforementioned lead removal apparatus and method is merely illustrative of the application of the principles of this invention and that numerous other arrangements may be devised by those skilled in the art without departing from the spirit and scope of the invention. In particular, a number of other control mechanisms may be attached to the proximal end of the stylet wire for operating the stylet wire in either a clockwise or counterclockwise direction as well as moving the wire longitudinally. Furthermore, this apparatus may be utilized for removing electrical leads from body ducts and passages as well as body tissue that has encapsulated the lead and restricted its movement.

What is claimed is:

1. A lead removal apparatus for removing an implanted lead from a patient, comprising:
   an elongated proximal portion capable of having both a first configuration and a second configuration; and
   a distal portion, connected to said proximal portion, including an expandable portion adapted to engage said implanted lead;
   wherein the first configuration includes a compacted, pre-formed shape, said compacted, pre-formed shape being constrainable into the second configuration, the second configuration being sufficiently straight in shape to permit passage thereover by a medical device having a passageway extending therethrough.

2. The lead removal apparatus of claim 1, wherein said elongated proximal portion is adapted to at least substantially reassume the first configuration once the proximal portion is no longer being constrained into the second configuration.

3. The lead removal apparatus of claim 1, wherein the first configuration of said elongated proximal portion comprises one or more coiled loops.

4. The lead removal apparatus of claim 3, wherein the first configuration comprises a plurality of coiled loops.

5. The lead removal apparatus of claim 1, wherein said elongated proximal portion has a length of about 30 cm or greater.

6. The lead removal apparatus of claim 5, wherein said elongated proximal portion has a length of about 40 cm or greater.

7. The lead removal apparatus of claim 6, wherein said elongated proximal portion has a length of about 60 cm or greater.

8. The lead removal apparatus of claim 7, wherein said elongated proximal portion has a length in the range of about 60–65 cm.

9. The lead removal apparatus of claim 1, wherein, said elongated proximal portion comprises a length of intertwined wire.

10. The lead removal apparatus of claim 1, wherein the expandable portion comprises a plurality of helically wound wires.

11. The lead removal apparatus of claim 10, further comprising an actuator portion adapted to deform the plurality of helically wound wires to effect the engaging of said implanted lead.

12. The lead removal apparatus of claim 11, wherein the actuator portion comprises a cannula slideably disposed over said lead removal apparatus.

13. A lead removal apparatus for removing an implanted lead from a patient, comprising:
an elongated proximal portion capable of having both a first configuration and a second configuration; and
a distal portion, connected to said proximal portion, including an expandable portion adapted to engage said implanted lead;
wherein the first configuration includes one or more coiled loops having a shape memory, said proximal portion having a shape memory being constrainable into the second configuration, the second configuration being sufficiently straight in shape to permit passage thereover by a medical device having a passageway extending therethrough.

14. The lead removal apparatus of claim 13, wherein said elongated proximal portion is adapted to at least substantially reassume the first configuration once the proximal portion is no longer being constrained into the second configuration.

15. The lead removal apparatus of claim 13, wherein the first configuration comprises a plurality of coiled loops.

16. The lead removal apparatus of claim 13, wherein said elongated proximal portion has a length of about 30 cm or greater.

17. The lead removal apparatus of claim 16, wherein said elongated proximal portion has a length of about 40 cm or greater.

18. The lead removal apparatus of claim 17, wherein said elongated proximal portion has a length of about 60 cm or greater.

19. The lead removal apparatus of claim 18, wherein said elongated proximal portion has a length in the range of about 60–65 cm.

20. The lead removal apparatus of claim 13, wherein, said elongated proximal portion comprises a length of intertwined wire.

21. The lead removal apparatus of claim 13, wherein the expandable portion comprises a plurality of helically wound wires.

22. The lead removal apparatus of claim 21, further comprising an actuator portion adapted to deform the plurality of helically wound wires to effect the engaging of said implanted lead.

23. The lead removal apparatus of claim 22, wherein the actuator portion comprises a cannula slideably disposed over said lead removal apparatus.

24. A lead removal apparatus for removing an implanted lead from a patient, comprising:
an elongated proximal portion comprising a length of intertwined wire measuring at least 40 cm, said elongated proximal portion capable of having both a first configuration and a second; and
a distal portion, connecting to said proximal portion, including an expandable portion adapted to engage said implanted lead;
wherein the first configuration includes a plurality of coiled loops having a shape memory, said plurality of coiled loops having a shape memory being constrainable into the second configuration, the second configuration being sufficiently straight in shape to permit passage thereover by a medical device having a passageway extending therethrough; and
wherein said elongated proximal portion has a tendency to resiliently reassume the first configuration once the proximal portion is no longer being constrained into the second configuration.

25. The lead removal apparatus of claim 24, wherein the expandable portion comprises a plurality of helically wound wires.

26. The lead removal apparatus of claim 25, further comprising an actuator portion adapted to deform the plurality of helically wound wires to effect the engaging of said implanted lead.

27. The lead removal apparatus of claim 26, wherein the actuator portion comprises a cannula slideably disposed over said lead removal apparatus.

28. A lead removal apparatus for removing an implanted lead from a patient, comprising:
an elongated proximal portion capable of having both a first configuration and a second configuration;
a distal portion, connected to said proximal portion, including expandable means for engaging said implanted lead; and
actuator means for activating the expandable means for effecting the engaging of said implanted lead;
wherein the first configuration includes a compacted, pre-formed shape, said compacted, pre-formed shape being constrainable into the second configuration, the second configuration being sufficiently straight in shape to permit passage thereover by a medical device having a passageway extending therethrough.

* * * * *

UNITED STATES PATENT AND TRADEMARK OFFICE
CERTIFICATE OF CORRECTION

PATENT NO. : 6,687,548 B2
DATED : February 3, 2004
INVENTOR(S) : Louis B. Goode

It is certified that error appears in the above-identified patent and that said Letters Patent is hereby corrected as shown below:

Column 32,
Line 22, delete "second;" and substitute -- second configuration; -- in its place.
Line 23, delete "connecting" and substitute -- connected -- in its place.

Signed and Sealed this

Tenth Day of August, 2004

JON W. DUDAS
*Acting Director of the United States Patent and Trademark Office*